(12) United States Patent
Kawai et al.

(10) Patent No.: US 8,877,024 B2
(45) Date of Patent: Nov. 4, 2014

(54) SENSOR CONTROL DEVICE AND SENSOR CONTROL METHOD

(75) Inventors: Takeshi Kawai, Komaki (JP); Hiroshi Inagaki, Komaki (JP); Koji Shiotani, Kasugai (JP); Hirotaka Onogi, Kakamigahara (JP); Satoshi Teramoto, Nisshin (JP)

(73) Assignee: NGK Spark Plug Co., Ltd., Aichi (JP)

( * ) Notice: Subject to any disclaimer, the term of this patent is extended or adjusted under 35 U.S.C. 154(b) by 453 days.

(21) Appl. No.: 12/957,641

(22) Filed: Dec. 1, 2010

(65) Prior Publication Data

US 2011/0132775 A1 Jun. 9, 2011

(30) Foreign Application Priority Data

Dec. 2, 2009 (JP) .................................. 2009-274514
Nov. 26, 2010 (JP) .................................. 2010-263658

(51) Int. Cl.
  *G01N 27/409* (2006.01)
  *G01N 27/417* (2006.01)

(52) U.S. Cl.
  USPC ........................................ 204/412; 205/784

(58) Field of Classification Search
  CPC .............. G01N 27/407; G01N 27/419; G01N 27/4065; F02D 41/146; F02D 41/1494; F02D 41/1454
  USPC .......... 204/410, 411, 421–429, 412; 205/781, 205/783.5–785, 787; 73/19.01–31.07; 219/201–208, 482–506
  See application file for complete search history.

(56) References Cited

U.S. PATENT DOCUMENTS

| 5,089,113 A * | 2/1992 | Logothetis et al. ............ 204/425 |
| 2009/0051373 A1* | 2/2009 | Kato et al. ..................... 324/693 |
| 2010/0140113 A1 | 6/2010 | Teramoto et al. |

FOREIGN PATENT DOCUMENTS

| JP | 2001-141696 A | 5/2001 |
| JP | 2001-281211 A | 10/2001 |

* cited by examiner

*Primary Examiner* — Luan Van
*Assistant Examiner* — Gurpreet Kaur
(74) *Attorney, Agent, or Firm* — Sughrue Mion, PLLC

(57) ABSTRACT

[Objective] An object is to provide a sensor control apparatus and a sensor-control-apparatus control method which can reduce variation in startup time among a plurality of times of execution of detection processing, in consideration of variation in output characteristic among a plurality of gas sensors. [Means for Solution] In a sensor control apparatus, before drive control (S55 to S80) is started, preliminary control is executed so as to supply a constant current to a second oxygen pump cell over a constant time, to thereby control to a constant level the amount of oxygen pumped from a second measurement chamber to the outside of the second measurement chamber (S40 to 50). The preliminary control is executed under control conditions of the sensor control apparatus which are determined for each gas sensor and are associated with the amount of oxygen pumped from the second measurement chamber to the outside thereof. The control conditions bring into a target range the concentration correspondence value calculated after start of the drive control which is started after the preliminary control is executed in a state in which a reference gas having a known concentration is introduced into the gas sensor.

7 Claims, 18 Drawing Sheets

SENSOR CONTROL DEVICE AND SENSOR CONTROL METHOD

TECHNICAL FIELD

The present invention relates to a sensor control apparatus which calculates a concentration correspondence value that represents the concentration of a specific gas contained in a gas to be detected (hereinafter referred to as an "object gas"), and to a method for controlling the sensor control apparatus.

BACKGROUND ART

Conventionally, there has been utilized a gas sensor which detects the concentration of a specific gas contained in an object gas such as exhaust gas. For example, an $NO_X$ sensor, which detects nitrogen oxides (hereinafter referred to as "$NO_X$") as a specific gas, includes an oxygen concentration detection cell, a first oxygen pump cell, and a second oxygen pump cell, each composed of an oxygen-ion conductive solid electrolyte layer and porous electrodes formed thereon. This $NO_X$ sensor operates as follows. The first oxygen pump cell pumps oxygen out of a first measurement chamber such that the oxygen concentration detection cell outputs a constant voltage, to thereby control the oxygen concentration of the object gas within the first measurement chamber to a constant level. Upon application of a constant voltage between the electrodes of the second oxygen pump cell, the second oxygen pump cell pumps oxygen out of the gas introduced from the first measurement chamber into a second measurement chamber (the gas whose oxygen concentration has been adjusted by the first oxygen pump cell). The concentration of $NO_X$ within the object gas is detected on the basis of a current flowing through the second oxygen pump cell as a result of application of the constant voltage thereto (hereinafter, processing of detecting the concentration of $NO_X$ within the object gas will be referred to as "detection processing").

In the case where the concentration of $NO_X$ contained in, for example, exhaust gas discharged from an internal combustion engine of an automobile is detected by use of an $NO_X$ sensor, the gas present in the second measurement chamber is becoming a lean state close to the atmosphere, in accordance with passage of time from the stoppage of the previous operation of the internal combustion engine to restart thereof. In view of such a phenomenon, some $NO_X$ sensors are configured to perform, at the time of startup of the internal combustion engine, preliminary control so as to temporarily and rapidly pump out oxygen present in the second measurement chamber and oxygen contained in a porous electrode facing the second measurement chamber, to thereby bring the interior of the second measurement chamber into a predetermined low-oxygen-concentration state. Thus, a time before stable measurement of the concentration of $NO_X$ contained in exhaust gas becomes possible is shortened. For example, the preliminary control is performed as follows. After a gas sensor element is started, a constant voltage higher than that in ordinary control is applied between the electrodes of the second oxygen pump cell so as to temporarily and rapidly pump out oxygen present in the second measurement chamber (see, for example, Patent Documents 1 and 2).

[Patent Document 1] Japanese Patent Application Laid-Open (kokai) No. 2001-281211
[Patent Document 2] Japanese Patent Application Laid-Open (kokai) No. 2001-141696

DISCLOSURE OF THE INVENTION

Problems to be Solved by the Invention

In general, there has been known a phenomenon that, when a voltage applied to the second oxygen pump cell is equal to or higher than a predetermined value, moisture ($H_2O$) contained in an object gas dissociates on the corresponding electrode of the second oxygen pump cell, and the current flowing between the electrodes of the second oxygen pump cell increases with the concentration of $H_2O$. That is, in the case where a constant voltage equal to or higher than the predetermined value is applied to the second oxygen pump cell, the amount of oxygen pumped out by the second oxygen pump cell changes depending on the $H_2O$ concentration. Therefore, in the case where a constant voltage higher than that in ordinary control is applied to the second oxygen pump cell at the time of startup of the internal combustion engine, there arises a problem in that startup time changes depending on the $H_2O$ concentration even when the same gas sensor is used. Notably, the startup time refers to a period of time between a point in time at which the gas sensor is started and a point in time at which stable detection of a value representing the concentration of $NO_X$ contained in the object gas becomes possible.

Furthermore, in some cases, a characteristic which represents the relation between the concentration of a specific gas and a concentration signal output from a gas sensor (hereinafter referred to as the "output characteristic") varies among gas sensors. For examples, the output characteristic may vary among a plurality of gas sensors even under the same $NO_X$ concentration due to product-to-product manufacturing variations (production tolerance). Therefore, there arises a problem in that, even in the case where the concentration of $H_2O$ contained in an object gas is constant, the startup time varies among the gas sensors, depending on their output characteristics.

The above-described problems occur not only in $NO_X$-sensors for detecting an $NO_X$ concentration correspondence value, but also in other gas sensors which detect concentrations of various specific gases by use of oxygen pump cells.

The present invention has been accomplished in the view of the above-described problems, and an object of the present invention is to provide a sensor control apparatus and a sensor-control-apparatus control method which can reduce variation in startup time of an individual gas sensor among a plurality of times of execution of detection processing, in consideration of variation in output characteristic among a plurality of gas sensors.

Means for Solving the Problems

In order to solve the above-described problems, a sensor control apparatus of the first mode comprises a gas sensor including a first measurement chamber into which an object gas is introduced, a first oxygen pump cell having a first solid electrolyte layer and paired first electrodes provided on the inside and outside, respectively, of the first measurement chamber, a second measurement chamber communicating with the first measurement chamber, and a second oxygen pump cell having a second solid electrolyte layer and paired second electrodes provided on the inside and outside, respectively, of the second measurement chamber; and a control section including a drive circuit section which performs drive control for adjusting an oxygen concentration of the object gas introduced into the first measurement chamber through supply of electricity to the first oxygen pump cell and for applying an ordinary voltage to the second oxygen pump cell, and calculation means for calculating a concentration correspondence value which represents a concentration of a specific gas, on the basis of the magnitude of current flowing through the second oxygen pump cell to which the ordinary voltage is applied. The sensor control apparatus is characterized in that the control section further includes preliminary control means for performing, before start of the drive control, preliminary control which supplies a constant current to the second oxygen pump cell over a constant time, to thereby control to a constant level an amount of oxygen pumped out from the second measurement chamber to the outside of the second measurement chamber; and the sensor control apparatus further includes storage means for storing control conditions of the sensor control apparatus which are associated with the amount of the pumped oxygen and are determined for the gas sensor individually, the control conditions being determined to bring into a target range the concentration correspondence value calculated by the calculation means after start of the drive control which is started after the preliminary control is executed in a state in which a reference gas having a known concentration is introduced into the gas sensor, wherein the preliminary control means executes the preliminary control under the control conditions.

The amount of oxygen pumped out by the second oxygen pump cell is in proportion to the current flowing between the paired second electrodes of the second oxygen pump cell. Therefore, in the sensor control apparatus of the first mode, at a point in time when the preliminary control ends, the oxygen concentration within the second measurement chamber becomes substantially the same level, irrespective of the concentration of $H_2O$ contained in the object gas, if the gas sensor is the same individual gas sensor. Furthermore in the sensor control apparatus of the first mode, the control conditions which adjust the amount of oxygen pumped out at the time of execution of the preliminary control are determined for each gas sensor. Therefore, the pattern which represents a change with time in the concentration correspondence value after the drive control is started in a state in which a reference gas having a known concentration is introduced into the gas sensor (hereinafter, this state may be referred to as "in the presence of a reference gas having a known concentration") falls within the target range. That is, since the control conditions which adjust the amount of oxygen pumped out at the time of execution of the preliminary control are set for each gas sensor individually, the sensor control apparatus can bring into the target range the concentration correspondence value calculated after start of the drive control, without being influenced by product-to-product manufacturing variations, etc. of the gas sensor. When the concentration correspondence value calculated after start of the drive control is compared among a plurality of gas sensors connected to respective sensor control apparatuses and which have different output characteristics, it is found that the change with time in the concentration correspondence value of each sensor control apparatus falls within the target range. The target range is properly determined in consideration of an allowable variation of the concentration correspondence value after start of the drive control. Accordingly, the sensor control apparatus of the first mode exhibits substantially the same pattern in terms of a change with time in the concentration correspondence value calculated after completion of the preliminary control (in other words, after start of the drive control), even when the $H_2O$ concentration of the object gas varies among a plurality of times of startup of the sensor control apparatus, or even when the output characteristic varies among the gas sensors. That is, the sensor control apparatus can reduce variation in startup time of the same individual gas sensor among a plurality of times of execution of the detection processing, in consideration of variation in output characteristic among the gas sensors. Moreover, the sensor control apparatus of the first mode can shorten the startup time by setting the target range in consideration of a predetermined range used to determine the end of the startup time, as compared with the case where preliminary control similar to the preliminary control of the sensor control apparatus of the first mode is not executed.

In the sensor control apparatus of the first mode, the control conditions may include at least one of the constant current and the constant time determined for each gas sensor. In this case, the sensor control apparatus can reduce variation in the concentration correspondence value after start of the drive control among the gas sensors by executing a simple control; i.e., controlling conditions under which electricity is supplied to the second oxygen pump cell at the time of execution of the preliminary control. In the case where the control conditions are set in such a manner that a time (constant time) over which electricity is supplied to the second oxygen pump cell is commonly set among the plurality of gas sensors, and the value of the constant current is set for each gas sensor in consideration of the output characteristic, the sensor control apparatus of the first mode can make the time from the startup to the execution of the drive control substantially the same among the gas sensors.

In the sensor control apparatus of the first mode may further comprise a heater for heating the gas sensor, and a heater control section which controls the supply of electricity to the heater, wherein the control conditions include a target heating temperature of the gas sensor determined for the gas sensor; and the preliminary control means controls the heater control section, to thereby control a temperature of the gas sensor to the target heating temperature set as the control conditions. In this case, the sensor control apparatus can reduce variation in the concentration correspondence value calculated after start of the drive control among the gas sensors by executing a simple control; i.e., controlling the temperature of the heater at the time of execution of the preliminary control. For example, in the case where the control conditions are set in such a manner that the time over which electricity is supplied to the second oxygen pump cell and the value of the current supplied thereto are commonly set among the plurality of gas sensors, and the value of the target heating temperature is set for each gas sensor individually in consideration of the output characteristic, the sensor control apparatus of the first mode can make the time from the startup to the execution of the drive control substantially the same among the gas sensors.

In the sensor control apparatus of the first mode, the storage means may further store, as correction data common among a plurality of gas sensors having the same configuration, pattern data which represents a change with time in the concentration correspondence value after the drive control is started after execution of the preliminary control in a state in which the reference gas having a known concentration is introduced into the gas sensor; and the control section may further include correction means for correcting the concentration correspondence value by use of the correction data after the drive control is started. In this case, the sensor control apparatus exhibits substantially the same pattern in terms of a change with time in the concentration correspondence value calculated after completion of the preliminary control, even when the $H_2O$ concentration of the object gas varies, or even when the output characteristic varies among the gas sensors. Accordingly, in the sensor control apparatus of the first mode, the corrected concentration correspondence value represents the concentration of a specific gas more early, as compared with the concentration correspondence value before being corrected. Accordingly, the sensor control apparatus of the first mode can shorten the startup period as compared with conventional apparatuses, and can accurately detect the concentration of the specific gas more early.

A sensor-control-apparatus control method of a second mode is a method of controlling a sensor control apparatus which comprises a gas sensor including a first measurement chamber into which an object gas is introduced, a first oxygen pump cell having a first solid electrolyte layer and paired first electrodes provided on the inside and outside, respectively, of the first measurement chamber, a second measurement chamber communicating with the first measurement chamber, and a second oxygen pump cell having a second solid electrolyte layer and paired second electrodes provided on the inside and outside, respectively, of the second measurement chamber; and a control section which executes a drive control step for adjusting an oxygen concentration of the object gas introduced into the first measurement chamber through supply of electricity to the first oxygen pump cell and for applying an ordinary voltage to the second oxygen pump cell, and a calculation step for calculating a concentration correspondence value which represents a concentration of a specific gas, on the basis of the magnitude of current flowing through the second oxygen pump cell to which the ordinary voltage is applied. The sensor-control-apparatus control method is characterized by comprising a preliminary control step of performing, before start of the drive control step, preliminary control which supplies a constant current to the second oxygen pump cell over a constant time, to thereby control to a constant level an amount of oxygen pumped out from the second measurement chamber to the outside of the second measurement chamber; and a read-out step of reading, out of storage means, control conditions of the sensor control apparatus which are associated with the amount of the pumped oxygen and are set for the gas sensor individually, the control conditions being determined to bring into a target range the concentration correspondence value calculated in the calculation step after start of the drive control which is started after the preliminary control is executed in a state in which a reference gas having a known concentration is introduced into the gas sensor, wherein in the preliminary control step, the preliminary control is executed under the control conditions. The sensor-control-apparatus control method of the second mode yields effects similar to those of the sensor control apparatus of the first mode.

MODE FOR CARRYING OUT THE INVENTION

Sensor control apparatuses according to first and second embodiments of the present invention will be described with reference to the drawings. Notably, the drawings which will be referred to are used only for the purpose of describing technical features which the present invention may employ, and the structure, etc. of an apparatus described therein are not intended to limit the present invention thereto and are mere explanatory examples.

Figure 1:
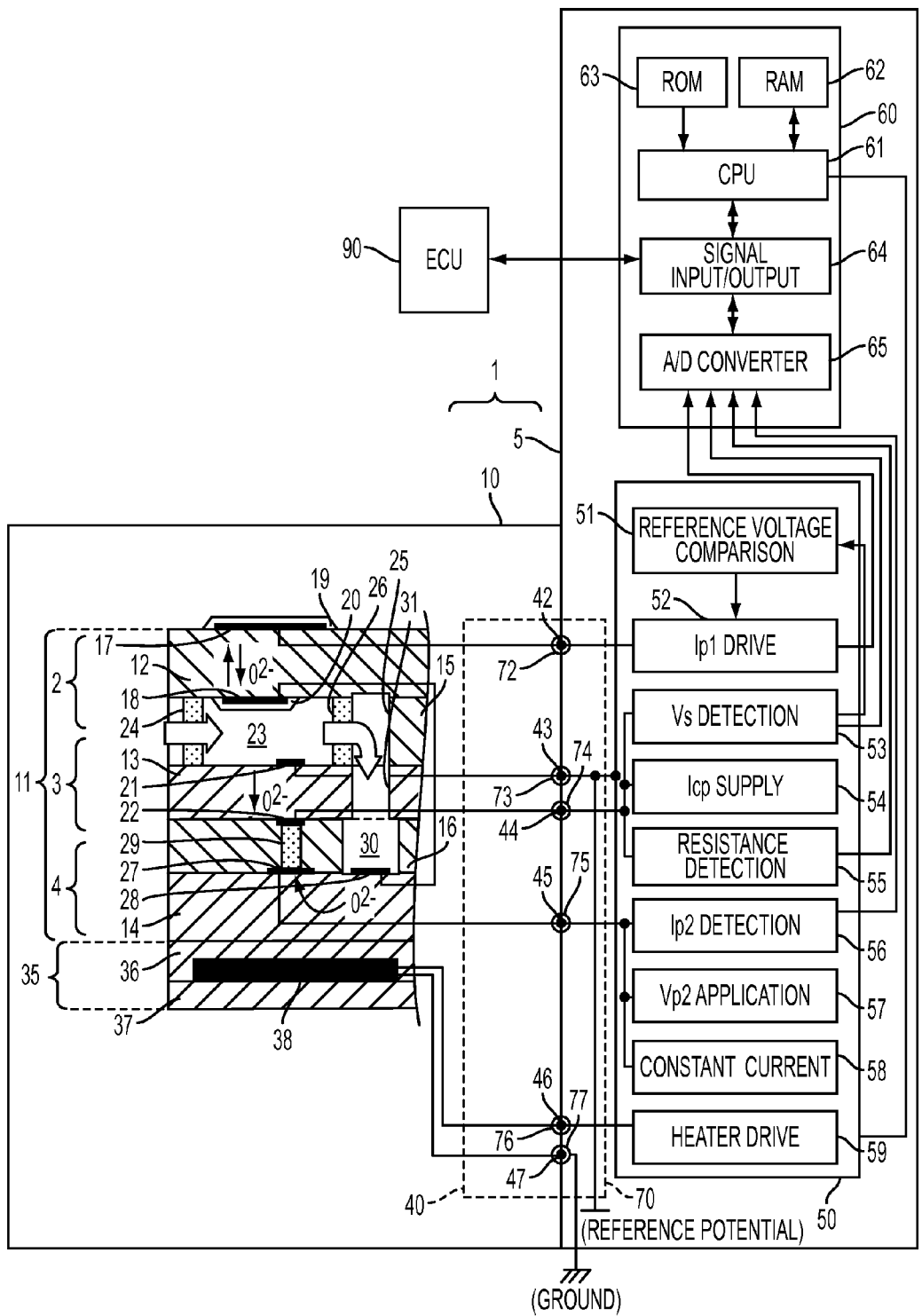
[FIG. 1] Conceptual diagram of a sensor control apparatus 1.

Sensor control apparatuses 1 of the first and second embodiments have the same physical and electrical configuration. Therefore, in the following, the sensor control apparatus 1 of the first embodiment will be described mainly. The sensor control apparatus 1 has a function of detecting the concentration of nitrogen oxides ($NO_X$) (specific gas). As shown in FIG. 1, the sensor control apparatus 1 includes a gas sensor 10 and a control section 5. The gas sensor 10 is attached to an exhaust passage (not shown) of an automobile, and outputs to the control section 5 a current value corresponding to the $NO_X$ concentration of exhaust gas. The control section 5, which is electrically connected to the gas sensor 10, controls the gas sensor 10, and calculates, on the basis of the current value output from the gas sensor 10, a concentration correspondence value representing the $NO_X$ concentration of the exhaust gas (hereinafter referred to as an "$NO_X$ concentration correspondence value"). The control section 5 of the present embodiment calculates the $NO_X$ concentration as the $NO_X$ concentration correspondence value. The gas sensor 10 and the control section 5 of the sensor control apparatus 1 will be described in detail.

The gas sensor 10 includes a detection element 11, a heater element 35, a connector section 40, and a housing (not shown). The detection element 11 has a layered structure formed by means of alternately laminating three platelike solid electrolyte bodies 12, 13, and 14, and insulating members 15 and 16 formed of alumina or the like. The heater element 35 is laminated on the solid electrolyte body 14 so as to quickly activate the solid electrolyte bodies 12 to 14 and stably maintain the activated states of the solid electrolyte bodies 12 to 14. The connector section 40 is connected to the detection element 11 and the heater element 35 via lead wires, and is provided for establishing electrical connection between the gas sensor 10 and the control section 5. The housing holds the detection element 11 and the heater element 35 therein so as to attach the gas sensor 10 to the exhaust passage (not shown). Next, the structures of various sections of the gas sensor 10 will be described in detail.

First, the structure of the detection element 11 will be described. The detection element 11 includes a first measurement chamber 23, a second measurement chamber 30, a reference oxygen chamber 29, a first oxygen pump cell 2 (hereinafter referred to as the "Ip1 cell 2"), an oxygen partial pressure detection cell 3 (hereinafter referred to as the "Vs cell 3"), and a second oxygen pump cell 4 (hereinafter referred to as the "Ip2 cell 4").

The first measurement chamber 23 is a small space within the detection element 11 into which exhaust gas within the exhaust passage is first introduced. The first measurement chamber 23 is formed between the solid electrolyte body 12 and the solid electrolyte body 13. An electrode 18 is disposed on a wall surface of the first measurement chamber 23 formed by the solid electrolyte body 12, and an electrode 21 is disposed on a wall surface of the first measurement chamber 23 formed by the solid electrolyte body 13. A first diffusion resistor 24 is provided in the first measurement chamber 23 to be located on the front end side of the detection element 11. The first diffusion resistor 24 functions as a partition between the interior and exterior of the first measurement chamber 23, and limits the amount (per unit time) of the exhaust gas flowing into the first measurement chamber 23. Similarly, a second diffusion resistor 26 is provided in the first measurement chamber 23 to be located on the rear end side of the detection element 11. The second diffusion resistor 26 functions as a partition between the first measurement chamber 23 and the second measurement chamber 30, and limits the amount (per unit time) of the gas flowing from the first measurement chamber 23 into the second measurement chamber 30.

The second measurement chamber 30 is a small space surrounded by the solid electrolyte body 12, the second diffusion resistor 26, the wall surface of an opening 25, the wall surface of an opening 31 provided in the solid electrolyte body 13, the insulating member 16, and an electrode 28. The second measurement chamber 30 communicates with the first measurement chamber 23. Exhaust gas whose oxygen concentration has been adjusted by the Ip1 cell 2 (hereinafter referred to as the "adjusted gas") is intruded into the second measurement chamber 30. The reference oxygen chamber 29 is a small space surrounded by the insulating member 16 and electrodes 22 and 27. A porous body formed of ceramic is placed in the reference oxygen chamber 29.

The Ip1 cell 2 includes the solid electrolyte body 12, and porous electrodes 17 and 18. The solid electrolyte body 12 is formed of, for example, zirconia, and has oxygen-ion conductivity. The electrodes 17 and 18 are provided on opposite sides of the solid electrolyte body 12 with respect to the lamination direction of the detection element 11. The electrodes 17 and 18 are formed of a material containing Pt as the main component. Examples of the material containing Pt as the main component includes Pt, Pt alloy, and cermet containing Pt and ceramic. Moreover, porous protection layers 19 and 20 formed of ceramic are formed on the surfaces of the electrodes 17 and 18, respectively. The solid electrolyte body 12 corresponds to the "first solid electrolyte layer" of the present invention, and the electrodes 17 and 18 correspond to the "paired first electrodes" of the present invention.

When a current is supplied between the two electrodes 17 and 18 of the Ip1 cell 2, the Ip1 cell 2 pumps oxygen (performs so-called oxygen pumping) between an atmosphere to which the electrodes 17 is exposed (the atmosphere outside the detection element 11) and an atmosphere to which the electrodes 18 is exposed (the atmosphere within the first measurement chamber 23).

The Vs cell 3 includes the solid electrolyte body 13, and porous electrodes 21 and 22. The solid electrolyte body 13 is formed of, for example, zirconia, and has oxygen-ion conductivity. The solid electrolyte body 13 is disposed to face the solid electrolyte body 12 with the insulating member 15 interposed therebetween. The electrodes 21 and 22 are provided on opposite sides of the solid electrolyte body 13 with respect to the lamination direction of the detection element 11. The electrode 21 is formed on the wall surface of the first measurement chamber 23 which faces the solid electrolyte body 12. The electrodes 21 and 22 are formed of the above-described material containing Pt as the main component.

The Vs cell 3 generates an electromotive force in accordance with mainly a difference in oxygen partial pressure between atmospheres partitioned by the solid electrolyte body 13 (between the atmosphere within the first measurement chamber 23, to which the electrode 21 is exposed, and the atmosphere within the reference oxygen chamber 29, to which the electrode 22 is exposed).

The Ip2 cell 4 includes the solid electrolyte body 14, and porous electrodes 27 and 28. The solid electrolyte body 14 is formed of, for example, zirconia, and has oxygen-ion conductivity. The solid electrolyte body 14 is disposed to face the solid electrolyte body 13 with the insulating member 16 interposed therebetween. The electrodes 27 and 28, which are formed of the above-described material containing Pt as the main component, are provided on a surface of the solid electrolyte body 14 facing the solid electrolyte body 13. The solid electrolyte body 14 corresponds to the "second solid electrolyte layer" of the present invention, and the electrodes 27 and 28 correspond to the "paired second electrodes" of the present invention.

The Ip2 cell 4 pumps oxygen between atmospheres partitioned by the insulating member 16 (between the atmosphere within the reference oxygen chamber 29, to which the electrode 27 is exposed, and the atmosphere within the second measurement chamber 30, to which the electrode 28 is exposed).

Next, the heater element 35 will be described. The heater element 35 includes insulating layers 36 and 37, and a heater conductor 38. The insulating layers 36 and 37 are mainly formed of alumina and assume a sheetlike shape. The heater conductor 38 is a single conductor sandwiched between the insulating layers 36 and 37 and extending within the heater element 35. One end of the heater conductor 38 is grounded, and the other end of the heater conductor 38 is connected to a heater drive circuit 59. The heater conductor 38 is formed of a material containing Pt as the main component.

Next, the connector section 40 will be described. The connector section 40 is provided on the rear end side of the gas sensor 10, and includes terminals 42 to 47. The electrode 17 is electrically connected to the terminal 42 via a lead wire. The electrodes 18, 21, and 28 are electrically connected to the terminal 43 via lead wires so that the electrodes 18, 21, and 28 assume the same potential. The electrode 22 is electrically connected to the terminal 44 via a lead wire. The electrode 27 is electrically connected to the terminal 45 via a lead wire. The heater conductor 38 is electrically connected to the terminals 46 and 47 via lead wires.

Next, the configuration of the control section 5 will be described. The control section 5 is an apparatus which controls the detection element 11 and the heater element 35 and which calculates an $NO_X$-concentration correspondence value on the basis of the current Ip2 obtained from the detection element 11, and outputs the calculated $NO_X$ concentration correspondence value to an ECU 90. The control section 5 includes a drive circuit section 50, a microcomputer 60, and a connector section 70. The drive circuit section 50 controls the detection element 11 and the heater element 35. The microcomputer 60 controls the drive circuit section 50. The connector section 70 is electrically connected to the connector section 40 of the gas sensor 10. In the following, the configurations of various parts of the control section 5.

The drive circuit section 50 includes a reference voltage comparison circuit 51, an Ip1 drive circuit 52, a Vs detection circuit 53, an Icp supply circuit 54, a resistance detection circuit 55, an Ip2 detection circuit 56, a Vp2 application circuit 57, a constant current circuit 58, and a heater drive circuit 59. Each of these circuits operates in accordance with a control signal from the microcomputer 60. Next, the configurations of the various circuits provided in the drive circuit section 50 will be described in detail.

The Icp supply circuit 54 supplies a weak current Icp between the electrodes 21 and 22 of the Vs cell 3 so as to pump oxygen from the first measurement chamber 23 into the reference oxygen chamber 29. The Vs detection circuit 53 detects a voltage (electromotive force) Vs between the electrodes 21 and 22, and outputs the detected voltage to the reference voltage comparison circuit 51. The reference voltage comparison circuit 51 compares the voltage Vs detected by the Vs detection circuit 53 with a reference voltage (e.g., 425 mV), and outputs the results of the comparison to the Ip1 drive circuit 52.

The Ip1 drive circuit 52 supplies a current Ip1 between the electrodes 17 and 18 of the Ip1 cell 2. The Ip1 drive circuit 52 adjusts the magnitude and direction of the current Ip1 on the basis of the results of the comparison performed by the reference voltage comparison circuit 51 for the voltage Vs between the electrodes 21 and 22 of the Vs cell 3, such that the voltage Vs substantially coincides with a previously set reference voltage. As a result, the Ip1 cell 2 pumps oxygen out of the first measurement chamber 23 to the outside of the detection element 11, or pumps oxygen into the first measurement chamber 23 from the outside of the detection element 11. In other words, through electricity supply control performed by the Ip1 drive circuit 52, the Ip1 cell 2 adjusts the oxygen concentration within the first measurement chamber 23 such that the voltage between the electrodes 21 and 22 of the Vs cell 3 is maintained at a constant value (the value of the reference voltage).

The resistance detection circuit 55 periodically supplies a current pulse having a prescribed magnitude to the Vs cell 3, and detects the amount of change in voltage (the amount of change in the voltage Vs) produced as a result of the supply of the current pulse. A value representing the amount of voltage change detected by the resistance detection circuit 55 is output to the microcomputer 60. The microcomputer 60 obtains the internal resistance (impedance) Rpvs of the Vs cell 3 on the basis of a table which is stored in the microcomputer 60 and represents the relation between the amount of change in the voltage Vs and the internal resistance Rpvs of the Vs cell 3. The internal resistance Rpvs of the Vs cell 3 has a correlation with the temperature of the Vs cell 3; that is, the temperature of the entire detection element 11. Therefore, the microcomputer 60 detects the temperature of the detection element 11 on the basis of the internal resistance Rpvs of the Vs cell 3. Notably, the configuration of the resistance detection circuit 55 for detecting the amount of voltage change representing the internal resistance Rpvs of the Vs cell 3 is known from, for example, Japanese Patent Application Laid-Open (kokai) No. H11-307458. Therefore, further description of the resistance detection circuit 55 will be omitted.

The Ip2 detection circuit 56 detects a current Ip2 flowing from the electrode 28 to the electrode 27 of the Ip2 cell 4. The Vp2 application circuit 57 applies an ordinary voltage Vp2 (e.g., 450 mV) between the electrodes 27 and 28 of the Ip2 cell 4 when drive control processing to be described later is performed, and controls pumping of oxygen from the second measurement chamber 30 into the reference oxygen chamber 29. The constant current circuit 58 supplies a current Ip3 of a constant magnitude (e.g., 10 µA) between the electrodes 28 and 27 of the Ip2 cell 4 when preliminary control processing to be described later is performed.

The heater drive circuit 59 maintains the solid electrolyte bodies 12, 13, and 14 (the gas sensor 10) at a predetermined temperature. The heater drive circuit 59 is controlled by the microcomputer 60, and supplies a current to the heater conductor 38 of the heater element 35 to thereby heat the solid electrolyte bodies 12, 13, and 14 (in other words, the Ip1 cell 2, the Vs cell 3, and the Ip2 cell 4). The heater drive circuit 59 can control the supply of current to the heater conductor 38 through PWM control such that the solid electrolyte bodies 12, 13, and 14 are heated to a target heating temperature. The heater drive circuit 59 corresponds to the "heater control section" of the present invention.

The microcomputer 60 is a known computation unit including a CPU 61, ROM 63, RAM 62, a signal input/output section 64, and an A/D converter 65. In accordance with previously stored programs, the microcomputer 60 outputs control signals to the drive circuit section 50 to thereby control the operations of the various circuits provided in the drive circuit section 50. The ROM 63 stores various programs, and various parameters which are referred at the time of execution of the programs. The ROM 63 in the second embodiment stores pattern data to be described later. The microcomputer 60 communicates, via the signal input/output section 64, with the ECU 90, which controls the internal combustion engine (not shown), and also communicates with the drive circuit section 50 via the A/D converter 65 and the signal input/output section 64.

The connector section 70 includes terminals 72 to 77. When the connector section 70 is connected to the connector section 40, the terminals 72 to 77 are connected to the terminals 42 to 47, respectively. The Ip1 drive circuit 52 is connected to the terminal 72 via wiring. The terminal 73 is connected to a reference potential via wiring. The Vs detection circuit 53, the Icp supply circuit 54, and the resistance detection circuit 55 are connected to the terminal 74 via wiring. The Ip2 detection circuit 56, the Vp2 application circuit 57, and the constant current circuit 58 are connected to the terminal 75 via wiring. The heater drive circuit 59 is connected to the terminal 76 via wiring. The terminal 77 is grounded via wiring.

Next, operation of the sensor control apparatus 1 for detecting $NO_X$ concentration will be described. Exhaust gas flowing through the exhaust passage (not shown) is introduced into the first measurement chamber 23 via the first diffusion resistor 24. At that time, the Icp supply circuit 54 supplies a weak current Icp to the Vs cell 3 such that the current Icp flows from the electrode 22 to the electrode 21. Therefore, oxygen contained in the exhaust gas flows, in the form of oxygen ions, from the electrode 21 (negative electrode) into the solid electrolyte body 13, and then moves into the reference oxygen chamber 29. That is, as a result of supply of the current Icp between the electrodes 21 and 22, oxygen within the first measurement chamber 23 is fed into the reference oxygen chamber 29.

The Vs detection circuit 53 detects the voltage Vs between the electrodes 21 and 22. The reference voltage comparison circuit 51 compares the detected voltage Vs with the reference voltage (e.g., 425 mV), and outputs the comparison result to the Ip1 drive circuit 52. Here, when the oxygen concentration within the first measurement chamber 23 is adjusted such that the potential difference between the electrodes 21 and 22 becomes constant in the vicinity of the reference voltage, the oxygen concentration of the exhaust gas within the first measurement chamber 23 approaches a predetermined concentration C (e.g., 0.001 ppm).

Therefore, when the oxygen concentration of the exhaust gas introduced into the first measurement chamber 23 is lower than the concentration C, the Ip1 drive circuit 52 supplies the current Ip1 to the Ip1 cell 2 such that the electrode 17 serves as a negative electrode. As a result, the Ip1 cell 2 pumps oxygen from the outside of the detection element 11 into the first measurement chamber 23. Meanwhile, when the oxygen concentration of the exhaust gas introduced into the first measurement chamber 23 is higher than the concentration C, the Ip1 drive circuit 52 supplies the current Ip1 to the Ip1 cell 2 such that the electrode 18 serves as a negative electrode. As a result, the Ip1 cell 2 pumps oxygen out of the first measurement chamber 23 to the outside of the detection element 11. At that time, the oxygen concentration of the exhaust gas can be detected on the basis of the magnitude and flow direction of the current Ip1.

The adjusted gas; i.e., the exhaust gas whose oxygen concentration has been adjusted to the concentration C in the first measurement chamber 23, is introduced into the second measurement chamber 30 via the second diffusion resistor 26. $NO_X$ which is contained in the adjusted gas and which comes into contact with the electrode 28 within the second measurement chamber 30 is decomposed (reduced) into $N_2$ and $O_2$ by the catalytic action of the electrode 28. The oxygen produced as a result of the decomposition receives electrons from the electrode 28, and becomes oxygen ions (dissociation), which flow through the solid electrolyte body 14 and move into the reference oxygen chamber 29. At that time, the value of the current Ip2 flowing between the paired electrodes 27 and 28 via the solid electrolyte body 14 corresponds to the $NO_X$ concentration, and the value of the current Ip2 is used for calculation of the $NO_X$ concentration correspondence value.

Next, the outline of main processing of the first embodiment shown in FIGS. 2A and 2B will be described. The main processing of the first embodiment includes activation processing (processing within a two-dot chain line 91), preliminary control processing (processing within a two-dot chain line 92), and drive control processing (processing within a two-dot chain line 93). The activation processing is processing of heating the detection element 11 by the heater element 35, to thereby activate the detection element 11. The control state of the sensor control apparatus 1 when the activation processing is being executed will be referred to as the "activation control." The preliminary control processing is processing of pumping a predetermined amount of oxygen from the second measurement chamber 30 before the drive control processing is executed. The control state of the sensor control apparatus 1 when the preliminary control processing is being executed will be referred to as the "preliminary control." The drive control processing is processing of adjusting, through supply of electricity to the Ip1 cell 2, the oxygen concentration of the exhaust gas introduced into the first measurement chamber 23, and applying the ordinary voltage Vp2 to the Ip2 cell 4. Furthermore, in the drive control processing, there is executed processing of calculating the $NO_X$ concentration correspondence value on the basis of the magnitude of the current of the Ip2 cell 4 to which the ordinary voltage Vp2 is applied. The control state of the sensor control apparatus 1 when the drive control processing is being executed will be referred to as the "drive control."

The gas filling the second measurement chamber 30 at the time of startup of the gas sensor 10 becomes lean in a period between a point in time when operation of the internal combustion engine was stopped during the previous execution of the main processing (i.e., when the supply of exhaust gas was stopped) and a point in time when the gas sensor 10 is started this time. In the case where the preliminary control is not executed, immediately after start of the drive control processing, the residual oxygen, etc. contained in the gas filling the second measurement chamber 30 before the start of that processing are pumped out from the second measurement chamber 30. In such a case, the current Ip2, which flows through the Ip2 cell 4, greatly changes in accordance with the residual oxygen, irrespective of the actual $NO_X$ concentration of the exhaust gas, which is to be calculated. Therefore, immediately after start of the drive control processing, the $NO_X$ concentration correspondence value based on the current Ip2 does not assume a value corresponding to the actual $NO_X$ concentration of the exhaust gas.

In order to solve such a problem, the sensor control apparatus 1 of the first embodiment executes the preliminary control processing prior to the drive control processing, to thereby lower the oxygen concentration within the second measurement chamber 30 (in a lean atmosphere state). However, as described above, in the case where a constant voltage equal to or greater than a predetermined value is applied to the Ip2 cell 4, the amount of oxygen pumped out by the Ip2 cell 4 changes depending on the $H_2O$ concentration of the gas within the second measurement chamber 30. In view of the above, in the first embodiment, during the preliminary control processing, the constant current circuit 58 is operated, so that the current supplied to the Ip2 cell 4 becomes constant. With this operation, if the same gas sensor 10 is used, every time the preliminary control processing is performed, substantially the same amount of oxygen can be pumped out from the second measurement chamber 30. In the first embodiment, the constant current Ip3 to be supplied to the Ip2 cell 4 at the time of the preliminary control is set to 10 μA. At that time, the voltage applied to the Ip2 cell 4 is greater than the ordinary voltage Vp2 (425 mV), which is the voltage applied to the Ip2 cell 4 during the drive control. Therefore, the amount of oxygen pumped out per unit time during the preliminary control is greater than that during the drive control.

Moreover, as described above, the output characteristic may vary among gas sensors 10 even when they have the same structure. Therefore, if the same control conditions are set for the different gas sensors 10, a change with time in the $NO_X$ concentration correspondence value immediately after start of the drive control processing (hereinafter referred to as a "changing pattern") may differ among the gas sensors 10. In view of this, in the first embodiment, the control conditions are set for each gas sensor 10 such that the $NO_X$ concentration correspondence value calculated after start of the drive control processing (in other words, after the end of the preliminary control) falls within a target range. The control conditions refer to conditions associated with the amount of oxygen pumped out from the second measurement chamber 30 during execution of the preliminary control. An example of the control conditions includes a combination of conditions selected from a target heating temperature of the gas sensor 10, and the electricity supply time and the value of constant current at the time of execution of the preliminary control. In the sensor control apparatus 1 of the first embodiment, of the parameters associated with the amount of oxygen pumped out from the second measurement chamber 30, the electricity supply time over which the constant current is supplied to the Ip2 cell 4 (preliminary control execution time) is set for each individual gas sensor 10. As to the remaining parameters, common values are set for the different gas sensors 10.

Figure 3:
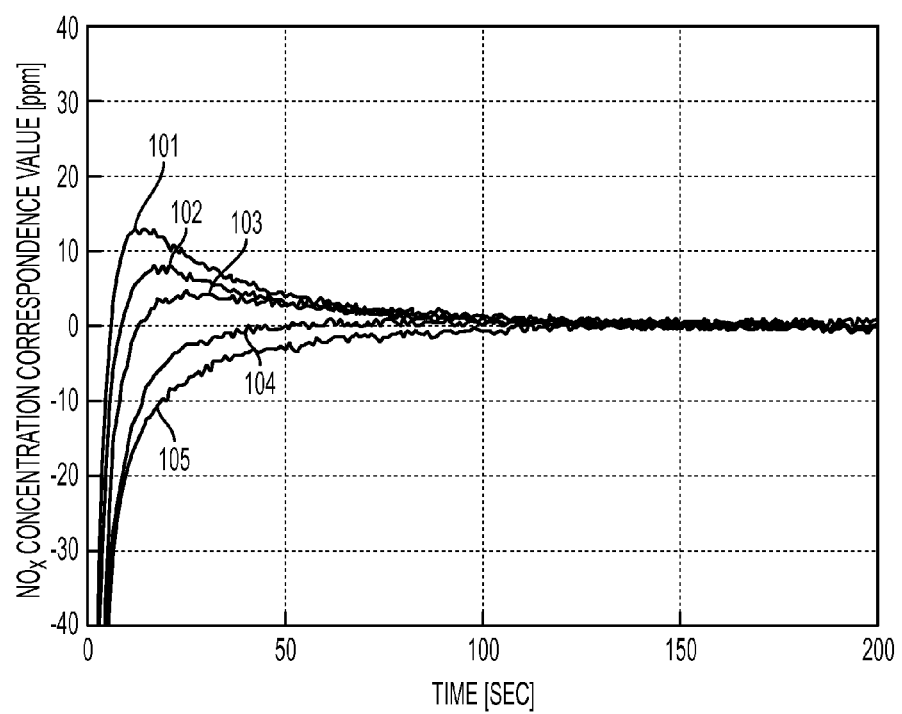
[FIG. 3] Graph representing changes with time in an $NO_X$ concentration correspondence value immediately after start of drive control for the case where the drive control was started after preliminary control was executed for the same gas sensor 10, while the time over which electricity was supplied to a second oxygen pump cell 4 was changed, and the current supplied to the second oxygen pump cell 4 and a target temperature of the gas sensor 10 heated by a heater element 35 were fixed.

The electricity supply time, which is contained in the control conditions, is set for each individual gas sensor 10 in accordance with the following procedure, for example. For preparation, by use of a predetermined number (e.g., 100) of gas sensors 10, a reference time and a target range are determined, and a comparison table is formed. The reference time is the time of the preliminary control which is performed in order to determine the electricity supply time contained in the control conditions. When the relation between the changing pattern and the electricity supply time in the preliminary control performed in the presence of the reference gas is compared among the gas sensors 10 having the same configuration, in general, the gas sensors 10 show the tendency that the shorter the electricity supply time during the preliminary control, the larger the concentration correspondence value immediately (e.g., 10 seconds) after start of the drive control processing. For example, FIG. 3 exemplifies, for a gas sensor 10 having the above-described configuration, the relation between the changing pattern and the electricity supply time during the preliminary control performed in the presence of the reference gas. Notably, in FIG. 3, the horizontal axis shows elapse of time after start of the drive control processing performed after the end of the preliminary control. As shown in FIG. 3, the $NO_X$ concentration correspondence value after passage of 25 sec from the start of the drive increases in the order of a pattern 101 (electricity supply time: 8 sec), a pattern 102 (electricity supply time: 9 sec), a pattern 103 (electricity supply time: 10 sec), a pattern 104 (electricity supply time: 20 sec), and a pattern 105 (electricity supply time: 50 sec). Notably, the reference gas refers to as a gas whose $NO_X$ concentration is known. Since a determination is made as to whether or not the $NO_X$ concentration correspondence value falls within a predetermined range (e.g., 0±5 ppm), preferably, the $NO_X$ concentration of the reference gas is 0 ppm. In the first embodiment, the composition of the reference gas was determined such that $NO_X$: 0 ppm; $O_2$: 7%, $H_2O$: 4%; and $N_2$ gas: balance. The temperature of the reference gas was set to 150° C.

Furthermore, although not illustrated, when the relation between the electricity supply time and variation in the $NO_X$ concentration correspondence value after start of the drive control processing is compared among a predetermined number of gas sensors 10, there is found a tendency that the shorter the electricity supply time, the greater the variation. In the case where the electricity supply time is set to be shorter than the reference time as in the first embodiment, the shorter the reference time, the greater the possibility that the variation in the electricity supply time among the gas sensors 10 increases and the startup time becomes longer. Accordingly, the reference time is determined in consideration of the variation among the gas sensors 10 and the startup time. In the first embodiment, the reference time is set to 20 sec. The target range is a range which is properly determined in consideration of an allowable range for the variation in the $NO_X$ concentration correspondence value after start of the drive control processing. Since the control conditions are set for each individual gas sensor 10, the $NO_X$ concentration correspondence value after start of the drive control processing assumes a value within the target range. Here, there is assumed a specific example in which a change with time in the $NO_X$ concentration correspondence value after execution of the preliminary control of the reference time was obtained for a predetermined number of gas sensors 10, and patterns represented by patterns 111 and 112 shown in FIG. 4 were obtained. In such a specific example, a target range 140 is set under the assumption that the control conditions are adjusted to make the pattern 112 approach the pattern 111.

The comparison table is a table which defines the relation between the electricity supply time and the $NO_X$ concentration correspondence value when the preliminary control of the reference time is executed. The comparison table is set on the basis of, for example, data which are similar to those shown in FIG. 3 and which are obtained for each of a predetermined number of gas sensors 10. When the sensor control apparatus 1 is manufactured, the electricity supply time is set for each gas sensor 10 on the basis of the comparison table and the $NO_X$ concentration correspondence value at the time when the drive control was executed after the preliminary control of the reference time was executed in the presence of the reference gas. The electricity supply time is stored in the ROM 63. In the above-described specific example, on the basis of the comparison table and the $NO_X$ concentration correspondence value after elapse of, for example, 30 seconds after start of the drive control processing performed after execution of the preliminary control of the reference time, 20 sec is set, as the electricity supply time, for a gas sensor 10 exhibiting the pattern 111 (hereinafter referred to as the "A-type gas sensor 10"), and 11 sec is set, as the electricity supply time, for a gas sensor 10 exhibiting the pattern 112 (hereinafter referred to as the "B-type gas sensor 10").

Next, the main processing of the first embodiment will be described with reference to FIGS. 2A and 2B. The CPU 61 executes the main processing upon receipt of an instruction from the ECU 90 at the time of startup of the internal combustion engine (not shown). Notably, the $NO_X$ concentration correspondence value calculated in the main processing is output to the ECU 90 at predetermined intervals in output processing, which is executed separately from the main processing, after the startup period is determined to have ended. In the output processing, the determination as to whether or not the startup period has ended is performed through determination as to whether or not a previously set time required for the $NO_X$ concentration correspondence value to fall within a predetermined range (e.g., 0±5 ppm) has elapsed.

When the internal combustion engine (not shown) is started and an instruction is fed from the ECU 90 to the signal input/output section 64, the CPU 61 obtains from the ROM 63 various conditions for executing the main processing (S5). In S5, for example, the electricity supply time at the time of the preliminary control set for each gas sensor 10 is read out as a control condition. Next, the CPU 61 executes the activation processing (S10 to S30). In the activation processing, the CPU 61 starts the supply of electricity to the heater conductor 38 of the gas sensor 10 (S10). Specifically, the CPU 61 applies a constant voltage (e.g., 12 V) to the heater conductor 38 by controlling the heater drive circuit 59.

Next, the CPU 61 starts the supply of the current Icp to the Vs cell 3 by controlling the Icp supply circuit 54 (S15). The Vs cell 3 supplied with the current Icp pumps oxygen from the first measurement chamber 23 into the reference oxygen chamber 29. As the internal resistance of the Vs cell 3 decreases as a result of the detection element 11 being heated by the heater element 35, the voltage Vs of the Vs cell 3 decreases gradually.

Next, the CPU 61 determines whether or not the voltage Vs obtained via the Vs detection circuit 53 is equal to or less than a predetermined value Vth (S20). When the voltage Vs is not equal to or less than the predetermined value Vth (S20: NO), the CPU 61 waits until the voltage Vs becomes equal to or less than the predetermined value Vth. When the voltage Vs is equal to or less than the predetermined value Vth (S20: YES), the CPU 61 starts to control the heater voltage Vh (S25). Specifically, the CPU 61 controls the supply of electricity to the heater element 35 via the heater drive circuit 59 such that the internal resistance Rpvs of the Vs cell 3 becomes equal to a target value. The target value is 300Ω, for example. When the internal resistance Rpvs is 300Ω, the temperature of the Vs cell 3 is estimated to be about 750° C.

Next, the CPU 61 determines whether or not the detection element 11 has been activated (S30). Specifically, the CPU 61 determines whether or not the detection element 11 has been activated, by determining whether or not the internal resistance Rpvs of the Vs cell 3 has reached a threshold value. The internal resistance Rpvs of the Vs cell 3 is calculated on the basis of the amount of change in the voltage Vs obtained via the resistance detection circuit 55, and a table which represents the previously determined relation between the amount of change in the voltage Vs and the internal resistance of the Vs cell 3. The threshold value is 350Ω, for example. When the internal resistance Rpvs is 350Ω, the temperature of the Vs cell 3 is estimated to be about 650° C. When the internal resistance Rpvs has reached the threshold, the CPU 61 determines that the detection element 11 has become activated.

When the detection element 11 has not yet become activated (S30: NO), the CPU 61 waits until the detection element 11 becomes activated. When the detection element 11 has become activated (S30: YES), the CPU 61 causes the Ip1 drive circuit 52 to operate, to thereby start the supply of electricity to the Ip1 cell 2 (S35). The supply of electricity to the Ip1 cell 2 is performed so as to adjust the oxygen concentration of the exhaust gas introduced into the first measurement chamber 23 to the predetermined concentration C.

Next, the CPU 61 executes the preliminary control processing (S40 to S50). In the preliminary control processing, the CPU 61 supplies a constant current to the Ip2 cell 4 over a constant electricity supply time set for each gas sensor 10 (S40). Specifically, the CPU 61 causes the constant current circuit 58 to operate, to thereby supply the constant current Ip3 to the Ip2 cell 4. The constant current Ip3 is 10 μA, for example. Upon receipt of the current Ip3, the Ip2 cell 4 starts the pumping of oxygen out of the second measurement chamber 30.

Next, the CPU 61 starts an unillustrated timer circuit (S45). The timer circuit is configured to time out after elapse of the electricity supply time. As described above, the electricity supply time is a value which is set for each individual gas sensor 10 and stored in the ROM 63. In the first embodiment, the electricity supply time is equal or shorter than the reference time (e.g., 20 sec). Next, the CPU 61 determines whether or not the electricity supply time has elapsed (a timeout has occurred) after the timer circuit was started (S50). When the timer circuit has not yet timed out (S50: NO), the CPU 61 continues the monitoring of the timer circuit (not shown). When the timer circuit has timed out (S50: YES), the CPU 61 ends the preliminary control processing, and switches the control of the Ip2 cell 4 to the drive control (S55). The CPU 61 stops the operation of the constant current circuit 58, and causes the Vp2 application circuit 57 to operate, to thereby switch the control state of the sensor control apparatus 1 from the preliminary control to the drive control. In the drive control, the ordinary voltage Vp2 (e.g., 450 mV) is applied to the Ip2 cell 4. In the drive control, the control of the supply of electricity to the Ip1 cell 2, which was started in S35, is executed continuously. Furthermore, in S55, timer processing for counting the time elapsed after start of the drive control is started. The timer processing is executed separately from the main processing. In the timer processing, a count value is incremented at predetermined time intervals, and the incremented count value is stored in the RAM 62.

Next, the CPU 61 obtains the value of the current Ip2 detected by the Ip2 detection circuit 56 (more specifically, a voltage obtained from the current Ip2 through current-voltage conversion), and stores in the RAM 62 the obtained value of the current Ip2 and the count value at the time of obtainment (S60). Next, the CPU 61 calculates the $NO_X$ concentration correspondence value, and stores the calculated $NO_X$ concentration correspondence value in the RAM 62 (S70). The $NO_X$ concentration correspondence value is calculated by, for example, applying the value of the current Ip2 to a predetermined formula stored in the ROM 63. Alternatively, with reference to a table which represents the relation between the value of the current Ip2 and the $NO_X$ concentration correspondence value, an $NO_X$ concentration correspondence value corresponding to the value of the current Ip2 obtained in S60 is calculated.

Next, when an end instruction is not received from the ECU 90 (S80: NO), the CPU 61 returns the processing to S60. When an end instruction is received from the ECU 90 (S80: YES), the CPU 61 ends the main processing.

As described above, the CPU 61 executes the main processing. Notably, the drive circuit section 50, which includes the reference voltage comparison circuit 51, the Ip1 drive circuit 52, the Vs detection circuit 53, the Icp supply circuit 54, and the Vp2 application circuit 57, functions as the drive circuit section of the present invention. The processing of S70 of FIGS. 2A and 2B corresponds to the calculation step of the present invention, and the CPU 61 which executes S70 functions as the calculation means of the present invention. The CPU 61, which executes S40 to S50, and the constant current circuit 58, which operates upon receipt of an instruction from the CPU 61, function as the preliminary control means of the present invention. The processing of S5 corresponds to the read-out step of the present invention. The processing of S55 to S80 corresponds to the drive control step of the present invention.

[Evaluation Test 1]

Next, there will be described Evaluation Test 1, which was performed so as to check whether or not the main processing of the first embodiment can reduce variation in startup time among a plurality of times of execution of the direction processing, in consideration of variation in the output characteristic among the gas sensors 10. In the test, there were used a sensor control apparatus 1 of Conventional Example and a sensor control apparatus 1 of Example, which included respective gas sensors 10 having the same structure. The $NO_X$ concentrations of a plurality of object gases having different $H_2O$ concentrations were measured by use of the sensor control apparatuses 1 of Conventional Example and Example. In the sensor control apparatus 1 of Conventional Example, the startup control was performed in accordance with a conventional method, and a change with time in the $NO_X$ concentration correspondence value was measured. In the sensor control apparatus 1 of Example, the startup control was performed in accordance with the main processing of the first embodiment, and a change with time in the $NO_X$ concentration correspondence value was measured. The composition of each object gas was determined such that $NO_X$: 0 ppm; $O_2$: 7%; $H_2O$: 0.5%, 4%, or 12%; $N_2$ gas (balance). The temperature of the object gas was set to 150° C.

Figure 5:
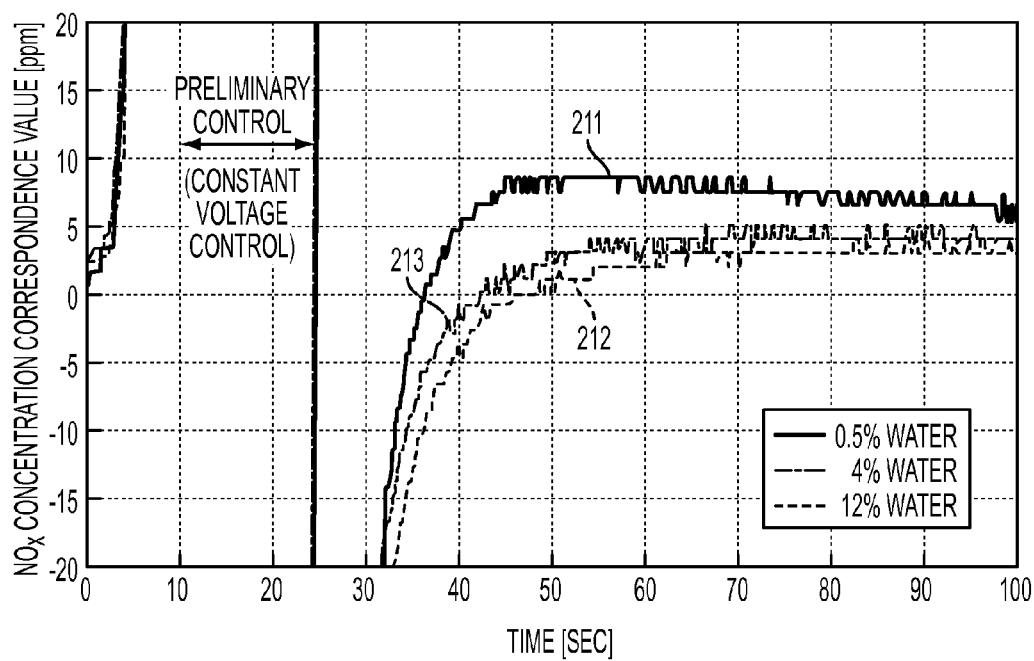
[FIG. 5] Graph representing changes with time of the $NO_X$ concentration correspondence value immediately after start of drive control for the case where the drive control was started after preliminary control was executed in a conventional manner.
Figure 6:
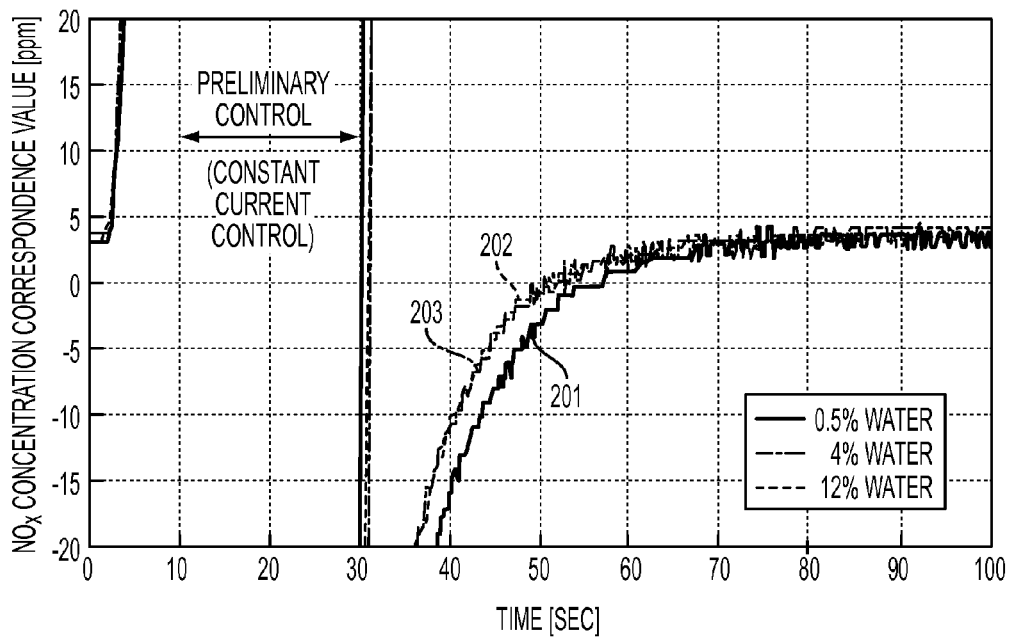
[FIG. 6] Graph representing changes with time of the $NO_X$ concentration correspondence value immediately after start of drive control for the case where the preliminary control was performed in accordance with the main processing of the first embodiment.

In the conventional startup control, the gas sensor 10 is activated about 10 sec after the supply of electricity to the heater conductor 38 is started after startup of the gas sensor 10, and the preliminary control is then started. After completion of the preliminary control, the control mode is switched to the drive control. In the conventional preliminary control, so-called constant-voltage control is executed, whereby a constant voltage (900 mV) is applied to the Ip2 cell 4 for a constant period of time (13 sec) (FIG. 5). Meanwhile, in the case of the main processing of the first embodiment, in the preliminary control, a constant current (10 μA) is supplied to the Ip2 cell 4 for a constant period of time (20 sec) (FIG. 6). In FIGS. 5 and 6, the horizontal axis represents the time elapsed after start of the gas sensor 10 (unit: sec), and the vertical axis represents the $NO_X$ concentration correspondence value (unit: ppm).

In Example and Conventional Example, as a result of the preliminary control, oxygen present in the second measurement chamber 30 is forcedly pumped into the reference oxygen chamber 29. Immediately after the switching from the preliminary control to the drive control, the oxygen concentration within the second measurement chamber 30 is lower than the reference concentration (rich atmosphere). As described above, as to the oxygen concentration within the second measurement chamber 30 at the time of the drive control, a concentration serving as a reference (reference concentration) is prescribed for the case where the voltage Vp2 is 450 mV. Therefore, immediately after the switching from the preliminary control to the drive control, the Ip2 cell 4 operates to pump oxygen from the reference oxygen chamber 29 into the second measurement chamber 30 such that the oxygen concentration within the second measurement chamber 30 becomes the reference concentration. As a result, after the preliminary control, the output $NO_X$ concentration correspondence value rises from the negative side as shown in FIGS. 5 and 6.

In the case of Conventional Example, as shown in FIG. 5, after completion of the preliminary control, a pattern 211 ($H_2O$ concentration=0.5%) rises more early with a greater rising slope, as compared with a pattern 212 ($H_2O$ concentration=4%) and a pattern 213 ($H_2O$ concentration=12%). As described above, in the case of Conventional Example, a variation arises among startup waveforms due to differences in the $H_2O$ concentration of the object gas. This phenomenon occurs for the following reason. At a point in time when the preliminary control ends, the higher the $H_2O$ concentration of the object gas, the lower the oxygen concentration within the second measurement chamber 30 (rich atmosphere). Therefore, there arises a difference in the pumping of oxygen from the reference oxygen chamber 29 back to the second measurement chamber 30 after completion of the preliminary control. Although not illustrated, when a constant voltage is applied to the Ip2 cell 4, the higher the $H_2O$ concentration of the object gas, the larger the current flowing through the Ip2 cell 4. Therefore, in the case where a constant voltage is applied to the Ip2 cell 4 for a constant period of time, the higher the $H_2O$ concentration of the object gas, the greater the amount of oxygen pumped out of the Ip2 cell 4.

Meanwhile, in the case of Example, as shown in FIG. 6, the slopes of a pattern 201 ($H_2O$ concentration=0.5%), a pattern 202 ($H_2O$ concentration=4%), a pattern 203 ($H_2O$ concentration=12%), as measured after completion of the preliminary control, substantially coincide with one another irrespective of the $H_2O$ concentration. In the case of Example, in the preliminary control, a constant current Ip3 (10 μA) is supplied to the Ip2 cell 4 for a constant time (20 sec). The Ip2 cell 4 pumps oxygen from the second measurement chamber 30 in an amount corresponding to the current flowing through the Ip2 cell 4. Therefore, when the constant current Ip3 is supplied to the Ip2 cell 4 as in the case of Example, the Ip2 cell 4 pumps a substantially constant amount of oxygen from the second measurement chamber 30, independently of the $H_2O$ concentration within the second measurement chamber 30. As a result, at a point in time when the preliminary control is ended, the oxygen concentration within the second measurement chamber 30 becomes substantially the same level irrespective of the $H_2O$ concentration. Therefore, no difference arises in the pumping of oxygen from the reference oxygen chamber 29 back to the second measurement chamber 30 after completion of the preliminary control. Through performance of Evaluation Test 1, it was confirmed that, when the preliminary control of Example is applied to the sensor control apparatus 1, startup waveforms become substantially the same, irrespective of differences in the $H_2O$ concentration of the object gas.

[Evaluation Test 2]

Figure 7:
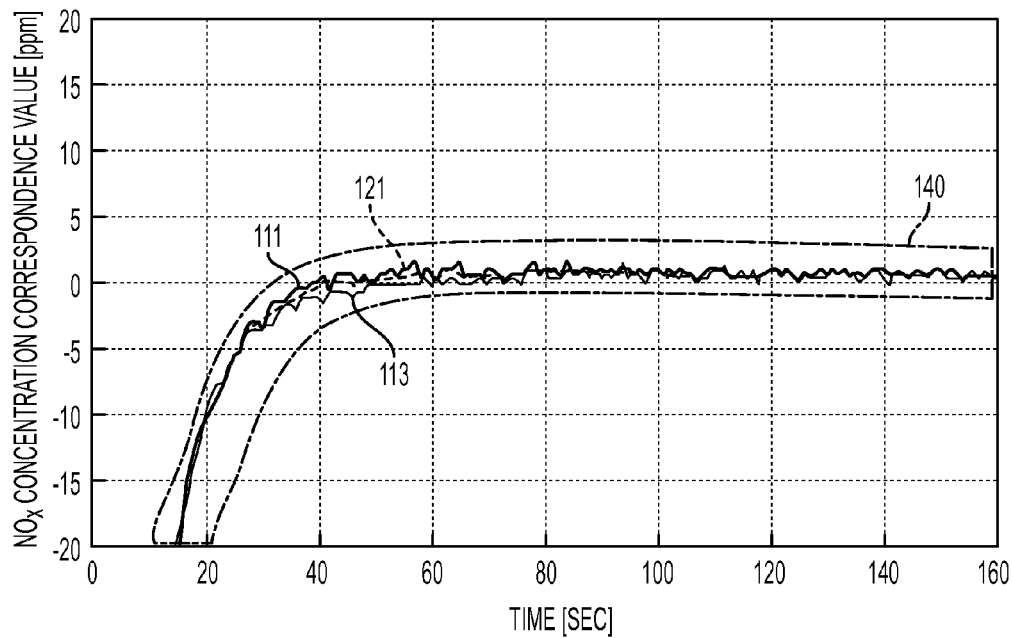
[FIG. 7] Graph representing changes with time of the $NO_X$ concentration correspondence value immediately after start of drive control for the case where control conditions (electricity supply time) is set for each gas sensor 10.

Next, it was checked whether or not a variation among gas sensors 10 in terms of the $NO_X$ concentration correspondence value after the preliminary control is improved by means of setting the electricity supply time at the time of the preliminary control for each individual gas sensor 10. Specifically, the $NO_X$ concentration of the reference gas having the above-described composition was measured by use of the above-described A-type and B-type gas sensors 10. Under the control conditions set for each gas sensor 10, the preliminary control was performed, and a change with time in the $NO_X$ concentration correspondence value after start of the drive control processing was calculated. FIG. 7 shows the results of Evaluation Test 2. In FIG. 7, the horizontal axis represents the time elapsed after start of the drive control processing (unit: sec), and the vertical axis represents the $NO_X$ concentration correspondence value (unit: ppm).

As shown in FIG. 7, the A-type gas sensor 10 exhibited a pattern 111, and the B-type gas sensor 10 exhibited a pattern 113. Both the pattern 111 and the pattern 113 rose from the negative side, and showed that the $NO_X$ concentration correspondence value sharply increased until 30 sec elapsed after start of the drive control processing, and decreased gently after that. Moreover, when 27 sec elapsed after start of the drive control processing, the $NO_X$ concentration correspondence value fell within a range of 0±5 ppm. Both the pattern 111 and the pattern 113 fell within the target range 140. The results of Evaluation Test 2 show that, by means of setting the control conditions for each gas sensor 10 (specifically, by means of setting the electricity supply time of the preliminary control for each gas sensor 10 while commonly setting the constant current Ip3 for all the gas sensors 10), the variation in the $NO_X$ concentration correspondence value immediately after start of the drive control processing after the preliminary control among the gas sensors 10 can be reduced.

Figure 4:
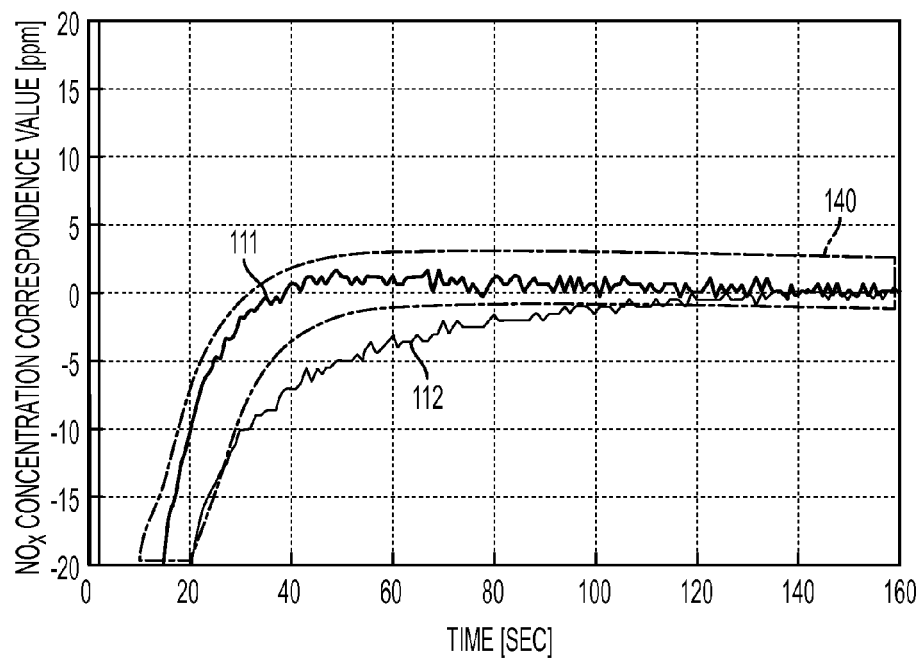
[FIG. 4] Graph representing changes with time of the $NO_X$ concentration correspondence value immediately after start of drive control for the case where preliminary control of a reference time was performed.

According to the sensor control apparatus 1 of the first embodiment having been described in detail, the following effects can be attained. The amount of oxygen pumped out by the Ip2 cell 4 is in proportion to the magnitude of the current flowing between the paired electrodes 27 and 28 of the Ip2 cell 4. Therefore, in the case of the sensor control apparatus 1, at a point in time when the preliminary control ends, the oxygen concentration within the second measurement chamber 30 becomes substantially the same level, irrespective of the concentration of $H_2O$ contained in the object gas, if the gas sensor 10 is the same individual gas sensor 10. Furthermore, in the sensor control apparatus 1, the control conditions for adjusting the amount of oxygen pumped at the time of the preliminary control is determined for each gas sensor 10 in consideration of the output characteristic of the gas sensor 10. By virtue of this configuration, even in the case where the sensor control apparatus 1 is used for a plurality of gas sensors 10 which have the same structure but differ in output characteristic as shown in FIG. 4, changing patterns of the gas sensors obtained when the drive control was started in the presence of a reference gas having a known concentration fall within the target range 140, as in the case of the patterns 111 and 113 of FIG. 7. Accordingly, even in the case where the $H_2O$ concentration of the object gas changes every time the sensor control apparatus 1 is started, and each gas sensor 10 has a different output characteristic (the output characteristic varies among the gas sensors 10), if the gas sensors 10 have the same configuration, they exhibit substantially the same pattern; i.e., substantially the same change with time in the $NO_X$ concentration correspondence value calculated after the end of the preliminary control (in other words, after start of the drive control). That is, the sensor control apparatus 1 can reduce variation in startup time among a plurality of times of execution of the detection processing for the same gas sensor 10, in consideration of variation in output characteristic among the gas sensor 10. Furthermore, in the sensor control apparatus 1, the target range 140 is set in consideration of a predetermined range (0±5 ppm) used for determining the end of the startup time. Therefore, the startup time can be shortened as compared with the case where preliminary control similar to that of the sensor control apparatus 1 is not executed. Moreover, since the electricity supply time set for each gas sensor 10 individually is used as the control conditions of the sensor control apparatus 1, variation in the $NO_X$ concentration correspondence value immediately after start of the drive control among the gas sensors 10 can be reduced by means of executing single control; i.e., controlling the electricity supply time.

Figure 8A:
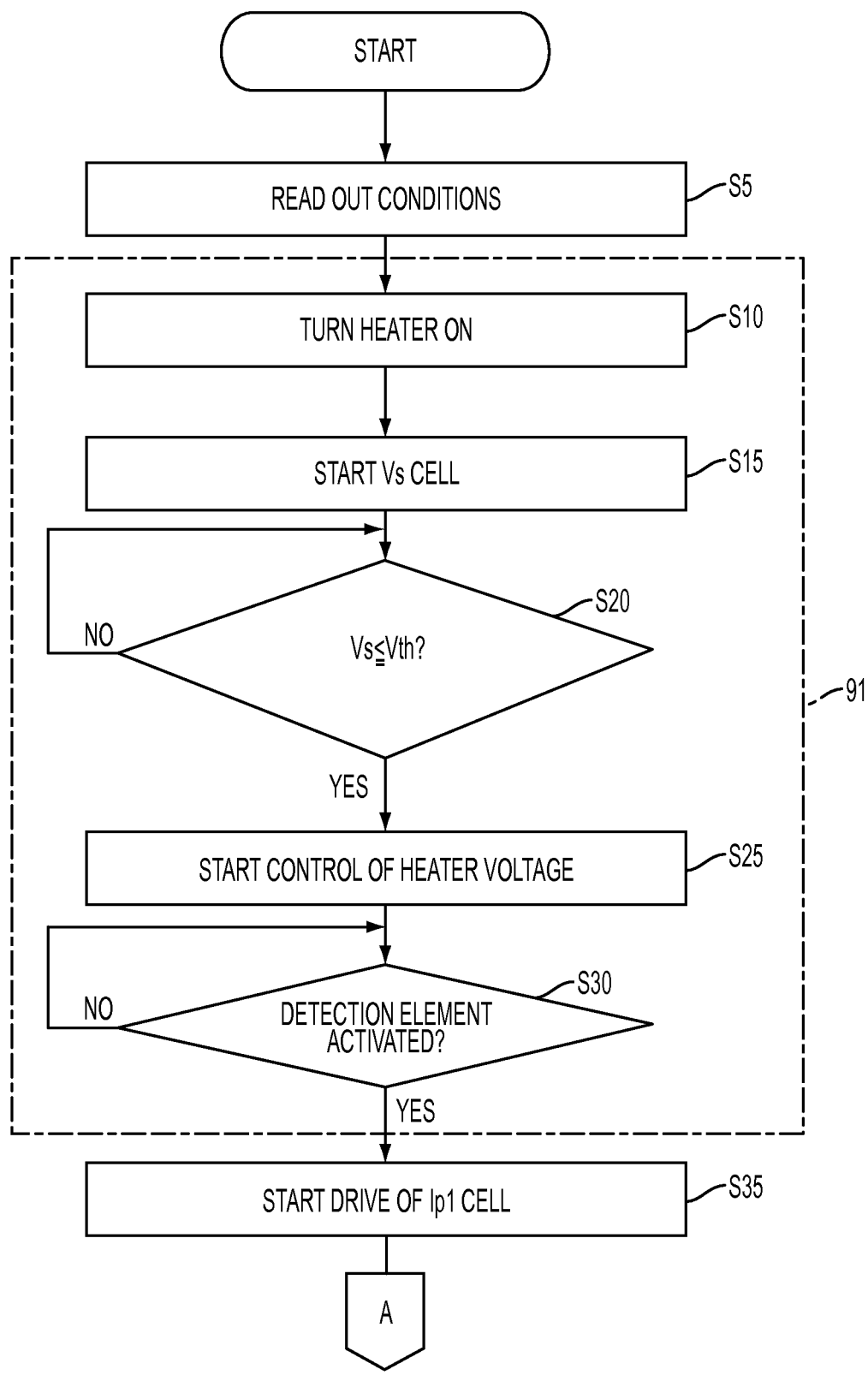
[FIGS. 8A and 8B] Flowchart of main processing according to a second embodiment.
Figure 8B:
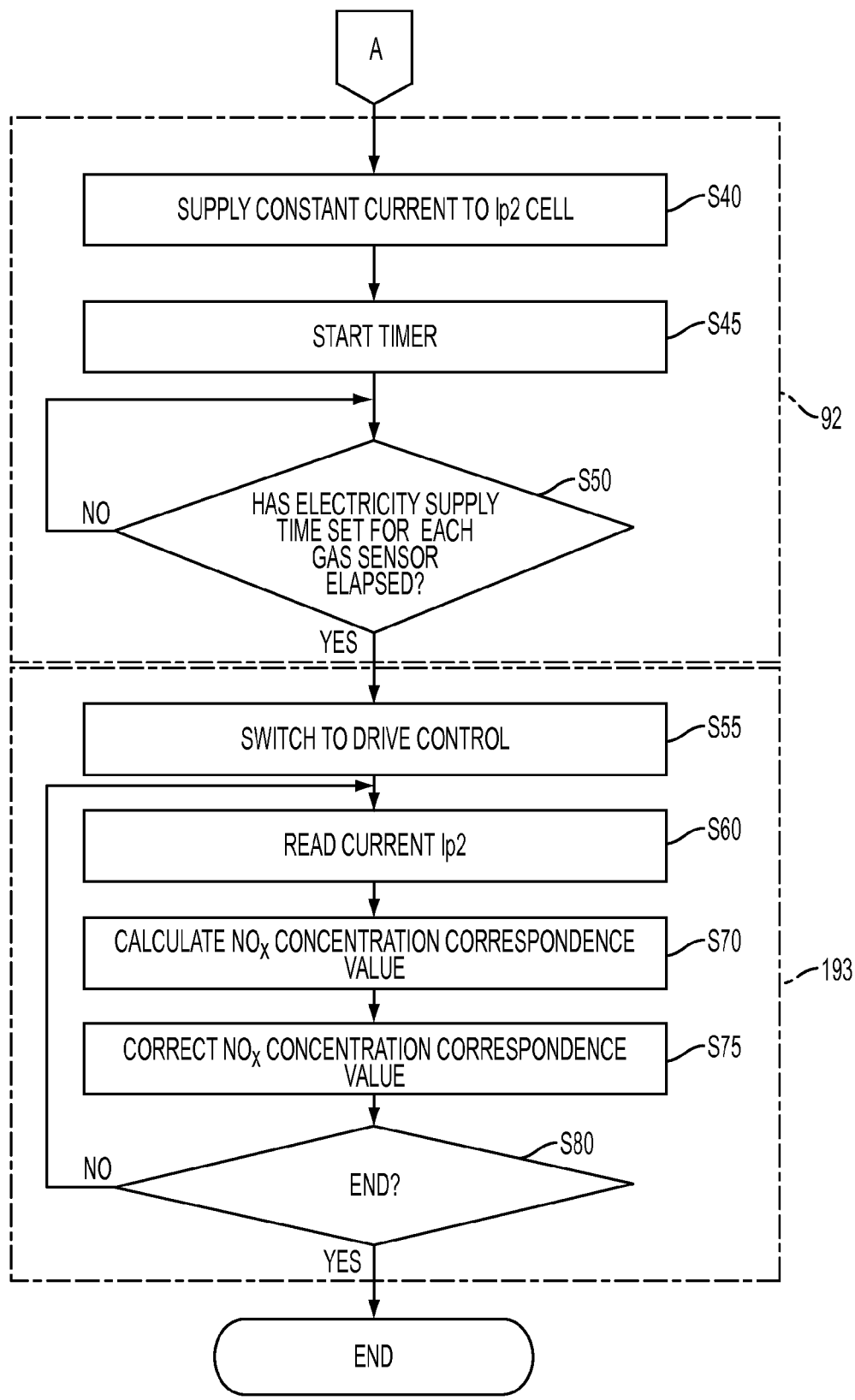

Incidentally, the $NO_X$ concentration correspondence value calculated by the main processing of the first embodiment falls within the target range when the gas sensor is used in the presence of a reference gas having a known concentration. That is, the $NO_X$ concentration correspondence value calculated by the main processing assumes substantially the same value, irrespective of variation among the gas sensors 10. Therefore, in the main processing, processing of correcting the $NO_X$ concentration correspondence value may be executed by use of pattern data as correction data common among the gas sensors 10 having the same structure. The pattern data refer to data which represent a change with time in the $NO_X$ concentration correspondence value after start of the drive control following the execution of the preliminary control in the presence of the reference gas. Next, the main processing of the second embodiment will be described with reference to FIGS. 8A and 8B. In FIGS. 8A and 8B, steps identical to the steps of the main processing of FIGS. 2A and 2B are denoted by the same step numbers.

The correction data are assumed to be stored in the ROM 63 of the control section 5. Correction data are data which represent a change with time in the $NO_X$ concentration correspondence value after start of the drive control following the execution of the preliminary control. Since the control conditions are set for each of gas sensors 10, if the gas sensors 10 have the same configuration, they exhibit substantially the same output characteristic; i.e., substantially the same changing pattern within the target range in the presence of the reference gas having a known concentration. In the present embodiment, data representing the pattern 121 shown in FIG. 7 are stored as the correction data.

Figure 2A:
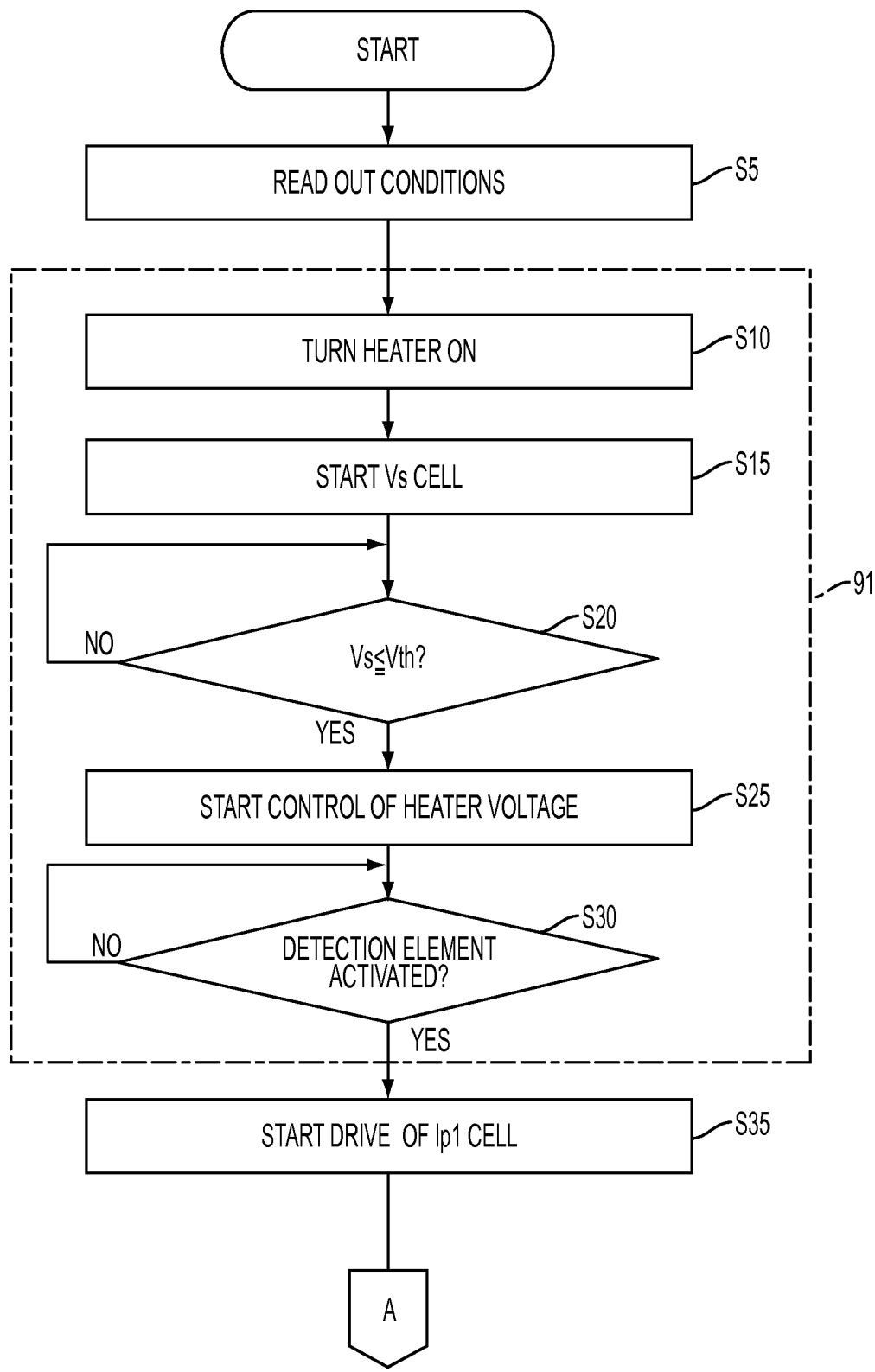
[FIGS. 2A and 2B] Flowchart of main processing according to a first embodiment.
Figure 2B:
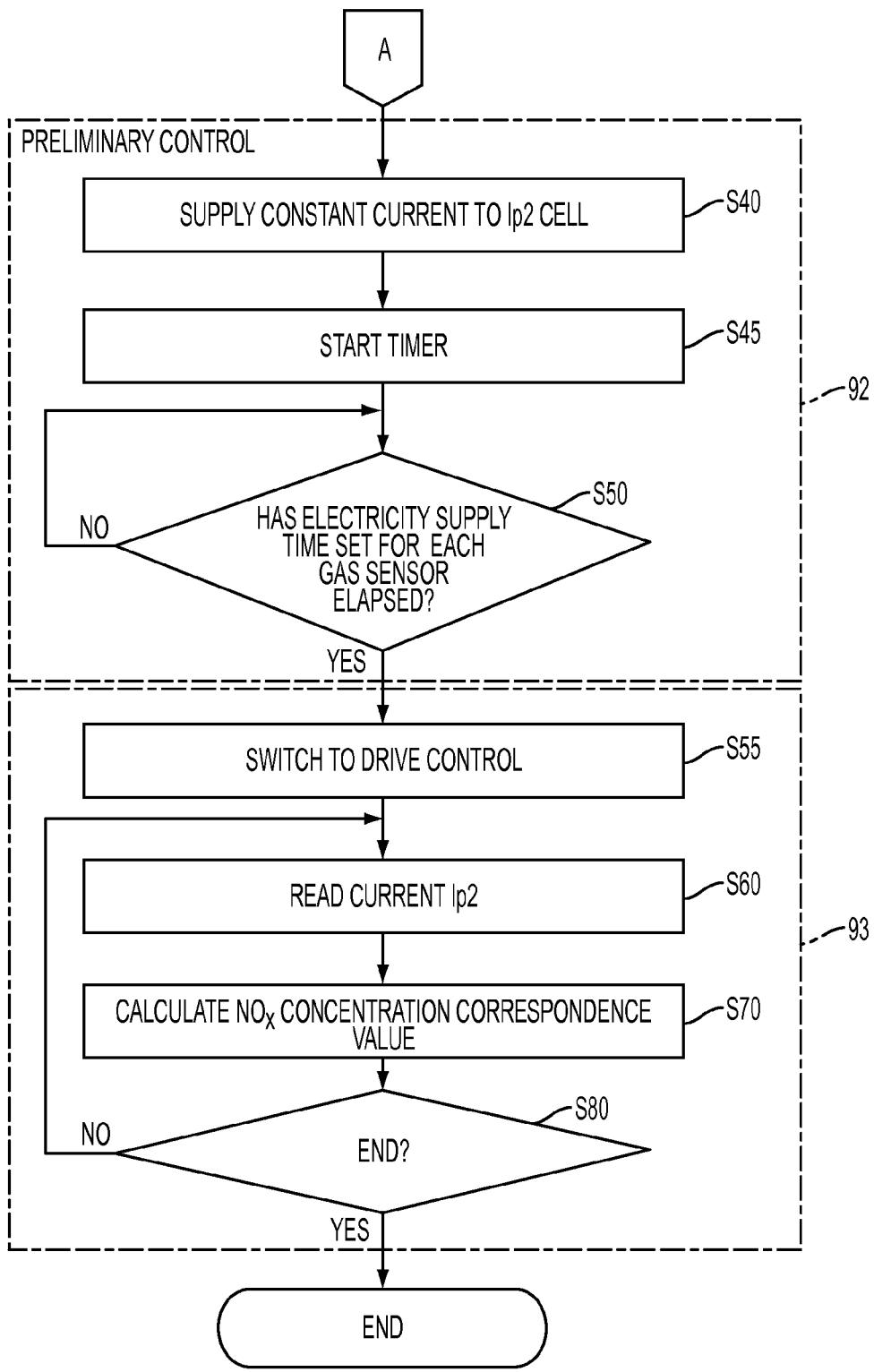

As shown in FIGS. 8A and 8B, the main processing of the second embodiment is identical with the main processing of the first embodiment shown in FIGS. 2A and 2B, except that processing of S75 is executed in the drive control processing (the processing within a two-dot chain line 193). Description of the same processing as the main processing of the first embodiment will not be repeated, and the processing of S75, which is not contained in the main processing of the first embodiment, will be described. When the internal combustion engine (not shown) is started, the CPU 61 executes the main processing in response to an instruction from the ECU 90.

In S75, the CPU 61 corrects the $NO_X$ concentration correspondence value calculated in S70, and stores the corrected $NO_X$ concentration correspondence value in the RAM 62. The $NO_X$ concentration correspondence value is corrected by a formula (the corrected $NO_X$ concentration correspondence value)=(the $NO_X$ concentration correspondence value calculated in S70)−(correction data corresponding to the time of acquisition of the value of the current Ip2). The correction data are stored in the ROM 63. The correction data corresponding to the time of acquisition of the value of the current Ip2 is a data set which is contained in the correction data and corresponds to the count value stored in the RAM 62 in S60.

The main processing of the second embodiment is executed as described above. The CPU 61, which executes the processing of S75 of FIGS. 8A and 8B, functions as the correction means of the present invention.

[Evaluation Test 3]

Figure 9:
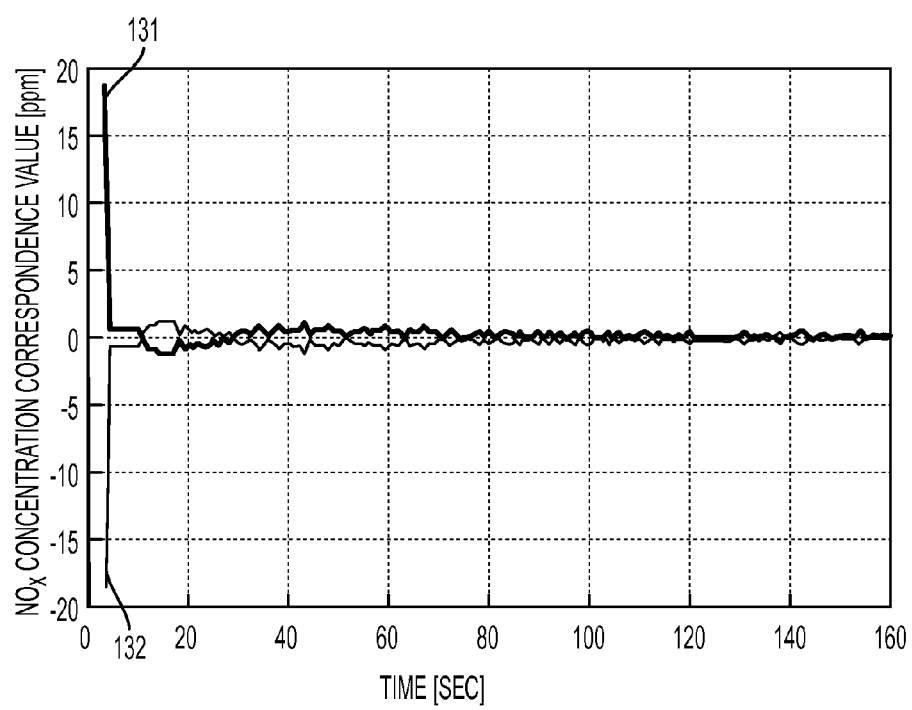
[FIG. 9] Graph exemplifying changes with time of the $NO_X$ concentration correspondence value corrected by use of correction data.

Next, there will be described an evaluation test which was performed in order to check the effect of the correction performed in the main processing of the second embodiment. In Evaluation Test 3, a change with time in the $NO_X$ concentration correspondence value after start of the drive control processing was calculated in the same manner as in the case of Evaluation Test 1, and the calculated $NO_X$ concentration correspondence value was corrected by use of the correction data. FIG. 9 shows the results of Evaluation Test 3. The vertical axis and the horizontal axis of FIG. 9 are the same as those of FIG. 7.

As shown in FIG. 9, the corrected $NO_X$ concentration correspondence value of the A-type gas sensor 10 is represented by a pattern 131, and the corrected $NO_X$ concentration correspondence value of the B-type gas sensor 10 is represented by a pattern 132. The pattern 131, which fell from the positive side, shows that the corrected $NO_X$ concentration fell within a range of ±1.2 ppm 2 seconds after start of the drive control processing. The pattern 132, which rose from the negative side, shows that the corrected $NO_X$ concentration fell within the range of ±1.2 ppm 2 seconds after start of the drive control processing. As shown in FIG. 7, in the case where correction is not performed, the sensor control apparatus 1 required about 27 seconds until the $NO_X$ concentration correspondence value fell within the range of 0±5 ppm after start of the drive control processing, and required about 35 seconds until the $NO_X$ concentration correspondence value fell within the range of 0±1.2 ppm after start of the drive control processing. It was confirmed that, through performance of the correction of the main processing of the second embodiment, the time between a point in time when the drive control processing is started and a point in time after which the $NO_X$ concentration correspondence value within the 0±5 ppm range can be stably obtained can be greatly shortened.

In the sensor control apparatus 1 of the second embodiment, the corrected $NO_X$ concentration correspondence value represents the concentration of a specific gas more early, as compared with the $NO_X$ concentration correspondence value before being corrected. Accordingly, the sensor control apparatus 1 can shorten the startup period, as compared with conventional apparatuses, by means of determining, whether or not the gas sensor 10 has started, by use of the corrected $NO_X$ concentration correspondence value. Thus, the sensor control apparatus 1 can accurately detect the concentration of the specific gas at an early stage.

Notably, the present invention is not limited to the above-described embodiments, and the embodiments may be modified in various manners without departing from the scope of the present invention. For example, the following modifications (1) to (6) are possible.

(1) In the above-described embodiments, the temperature of the detection element 11 is detected on the basis of the internal resistance of the Vs cell 3. However, the temperature of the detection element 11 may be detected on the basis of the internal resistance of the Ip1 cell 2 or the Ip2 cell 4. Alternatively, the temperature of the detection element 11 may be detected on the basis of the resistance of the heater conductor 38, which constitutes the heater element 35.

(2) In the above-described embodiments, $NO_X$ sensors for detecting the concentration of $NO_X$ are exemplified. However, the sensor control apparatus of the first mode can be applied to various gas sensors constituted by use of solid electrolyte bodies (e.g., oxygen sensor).

(3) The configuration of the sensor control apparatus 1 of the above-described embodiments may be changed freely. For example, the configuration of the drive circuit section of the control section 5 may be changed freely. The control section 5 and the gas sensor 10 may be unitarily configured such that they cannot be separated from each other. The sensor control apparatus of the first mode may be applied to a gas sensor which includes an atmospheric-air introduction hole in place of the reference oxygen chamber 29. The location and/or the type of the storage device in which the control conditions and the correction data are stored can be changed freely, so long as the control conditions and the correction data are stored in any of the storage devices provided in the sensor control apparatus 1. Therefore, a storage device may be provided in the connector section 40 of the gas sensor 10, and the control conditions may be stored in this storage device. In this case, in the main processing, the control conditions are read out of the storage device provided in the connector section 40.

Figure 10A:
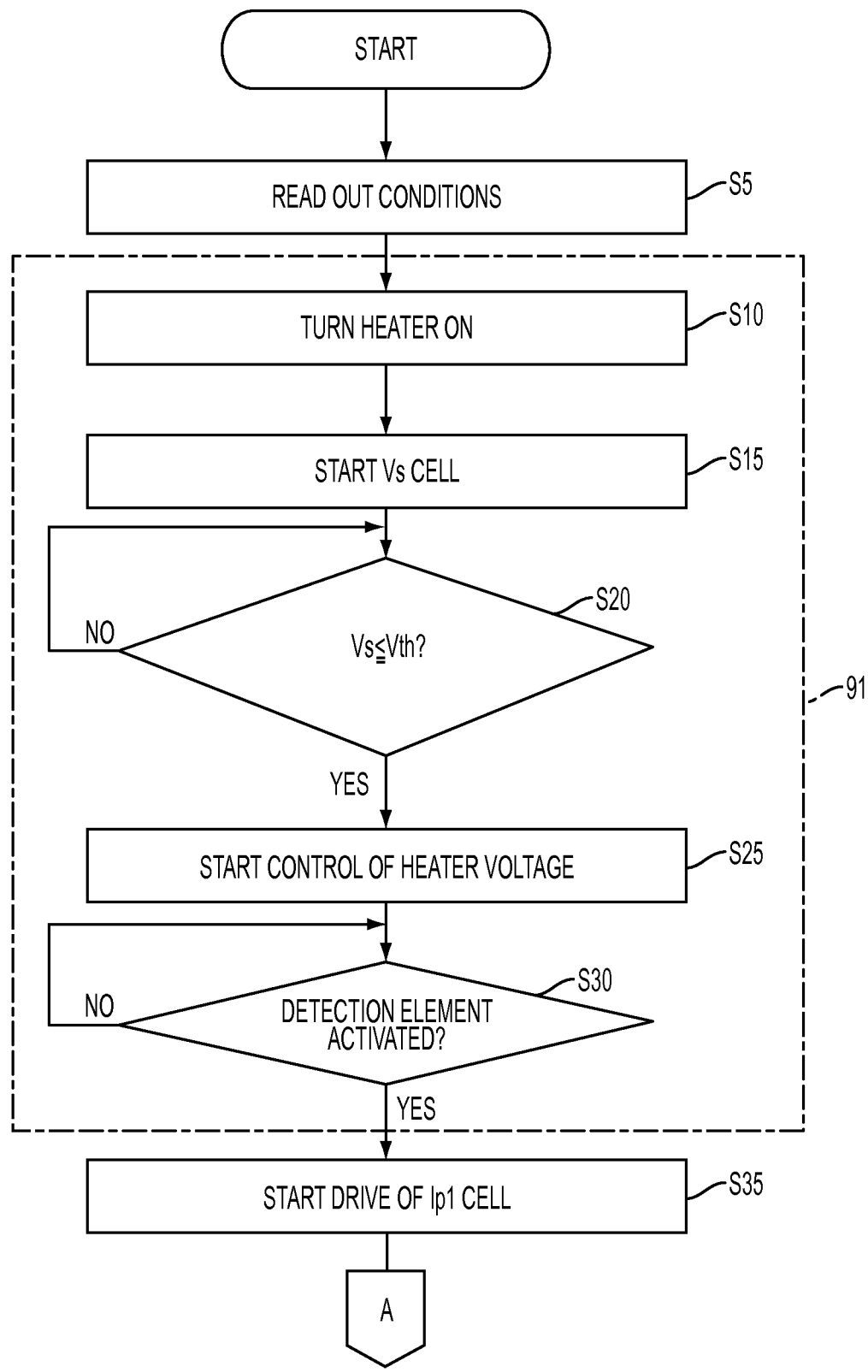
[FIGS. 10A and 10B] Flowchart of main processing according to a modification.
Figure 10B:
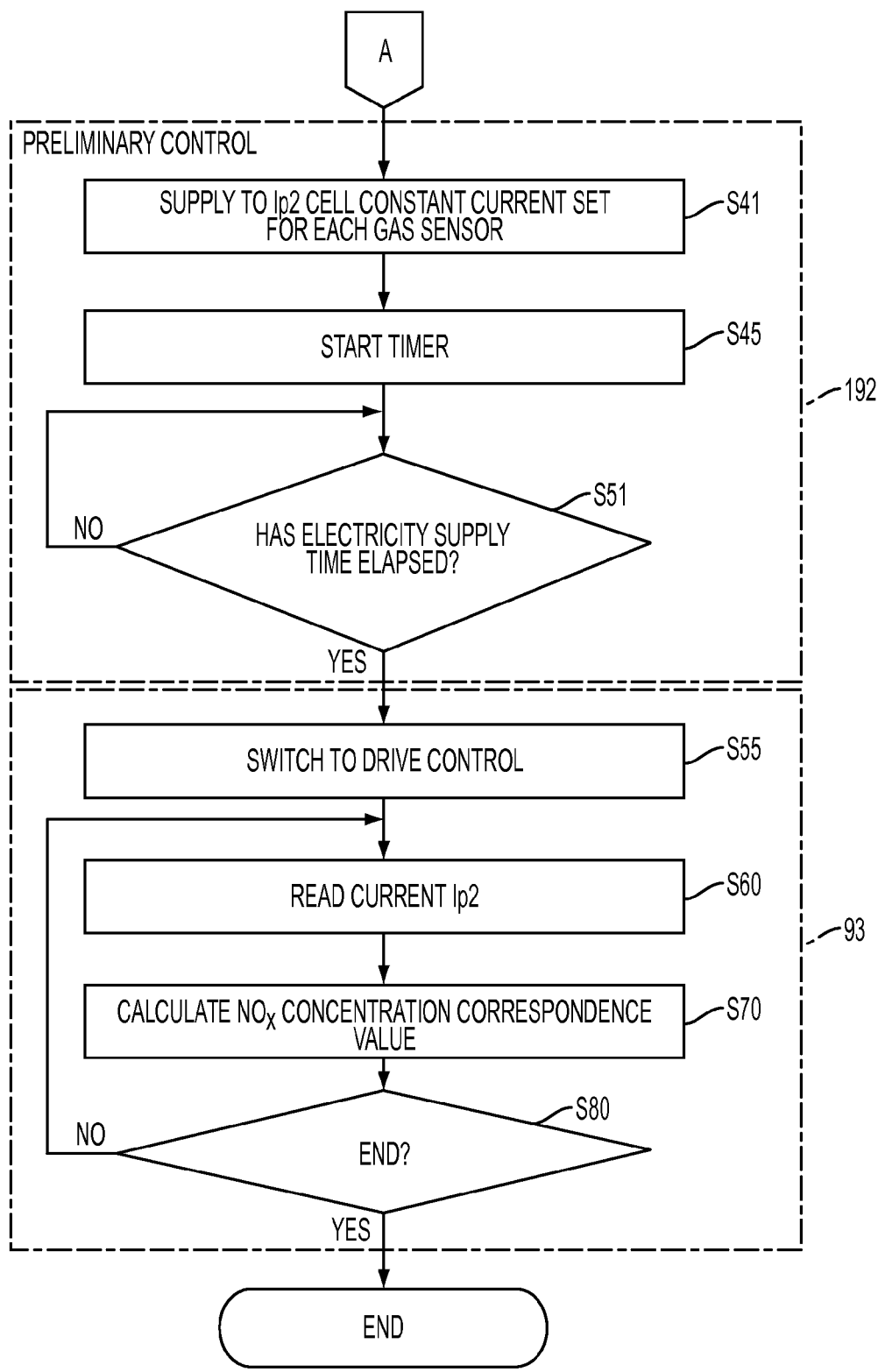

(4) The control conditions may be changed properly. An example of the control conditions set for each gas sensor 10 may be a combination of conditions selected from the constant current and the electricity supply time used in the preliminary control, and the target heating temperature of the gas sensor 10. In the case where control conditions are set in such a manner that the target heating temperature and the electricity supply time at the time of the preliminary control are set, as common control conditions, for all the gas sensors 10, and the value of the constant current is set for each gas sensor, the following processing may be executed, for example, in the main processing shown in FIGS. 10A and 10B. In FIGS. 10A and 10B, steps identical to the steps of the main processing of FIGS. 2A and 2B are denoted by the same step numbers. The main processing of FIGS. 10A and 10B differs from the main processing of FIGS. 2A and 2B in S41 and S51 of the preliminary control processing within a two-dot chain line 192. Description of the steps of the main processing of FIGS. 10A and 10B similar to those of the main processing of FIGS. 2A and 2B will be omitted. In S41, the constant current set for each gas sensor 10 is supplied. In S51, the CPU 61 waits until the electricity supply time commonly set among the gas sensors 10 elapses after the timer circuit was started in S45 (S51: NO). When the electricity supply time has elapsed after the timer circuit was started (S51: YES), the CPU 61 executes the drive control processing.

[Evaluation Test 4]

Figure 11:
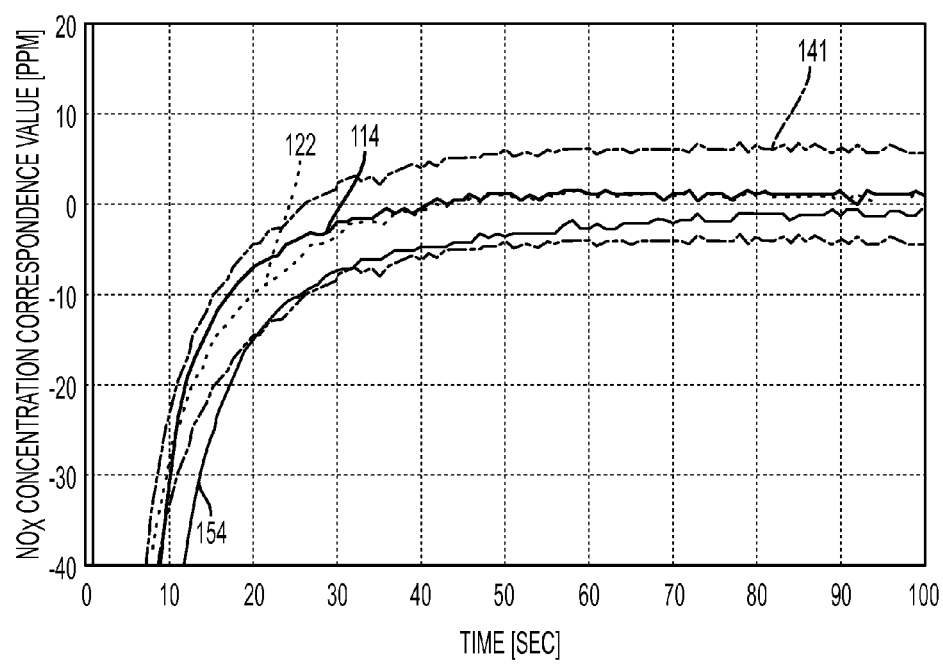
[FIG. 11] Graph representing changes with time of the $NO_X$ concentration correspondence value immediately after start of drive control for the case where preliminary control was performed under control conditions of Evaluation Test 4.

It was checked whether or not the changing pattern can be made closer to the reference pattern by means of setting the control conditions in such a manner that the value of the constant current at the time of the preliminary control is set for each gas sensor 10, and the constant electricity supply time at the time of the preliminary control and the target heating temperature are commonly for the gas sensors 10. The reference pattern is a changing pattern used as a reference for setting the target range. The electricity supply time at the time of the preliminary control was set to 20 seconds, and the target value of the internal resistance Rpvs of the Vs cell 3 was set to 300Ω. An example in which the constant current was set to 10 µA, which was the same as that in the above-described embodiments, was called Comparative Example, and an example in which the constant current at the time of the preliminary control was set to 3 µA to be suited for the gas sensor 10 was called Example. The reference gas having the above-described composition was measured by use of the same gas sensor 10, while the preliminary control was performed under the control conditions of Comparative Example or those of Example, and a change with time in the $NO_X$ concentration correspondence value after start of the drive control processing was calculated. FIG. 11 shows the results of Evaluation Test 4. In FIG. 11, the horizontal axis represents the time elapsed after start of the drive control processing (unit: sec), and the vertical axis represents the $NO_X$ concentration correspondence value (unit: ppm).

As shown FIG. 11, in Evaluation Test 4, the target range 141 was set to a ±5 ppm range of the reference pattern 122. Both the pattern 154 of Comparative Example and the pattern 114 of Example rose from the negative side, and showed that the $NO_X$ concentration correspondence value sharply increased until 30 sec elapsed after start of the drive control processing, and increased gently after that. In the case of Comparative Example, 21 sec was required for the $NO_X$ concentration correspondence value to fall within the target range 141. In contrast, in the case of Example, 11 sec was required for the $NO_X$ concentration correspondence value to fall within the target range 141. That is, like the pattern 114 of Example, the pattern 154 of Comparative Example can be made closer to the reference pattern 122 by means of setting the value of the constant current of the preliminary control for each gas sensor 10. The results of Evaluation Test 4 show that, by means of setting the control conditions for each gas sensor 10 (specifically, by means of setting the value of the constant current of the preliminary control for each gas sensor 10), the variation in the $NO_X$ concentration correspondence value immediately after start of the drive control processing after the preliminary control among the gas sensors 10 can be reduced.

Figure 12A:
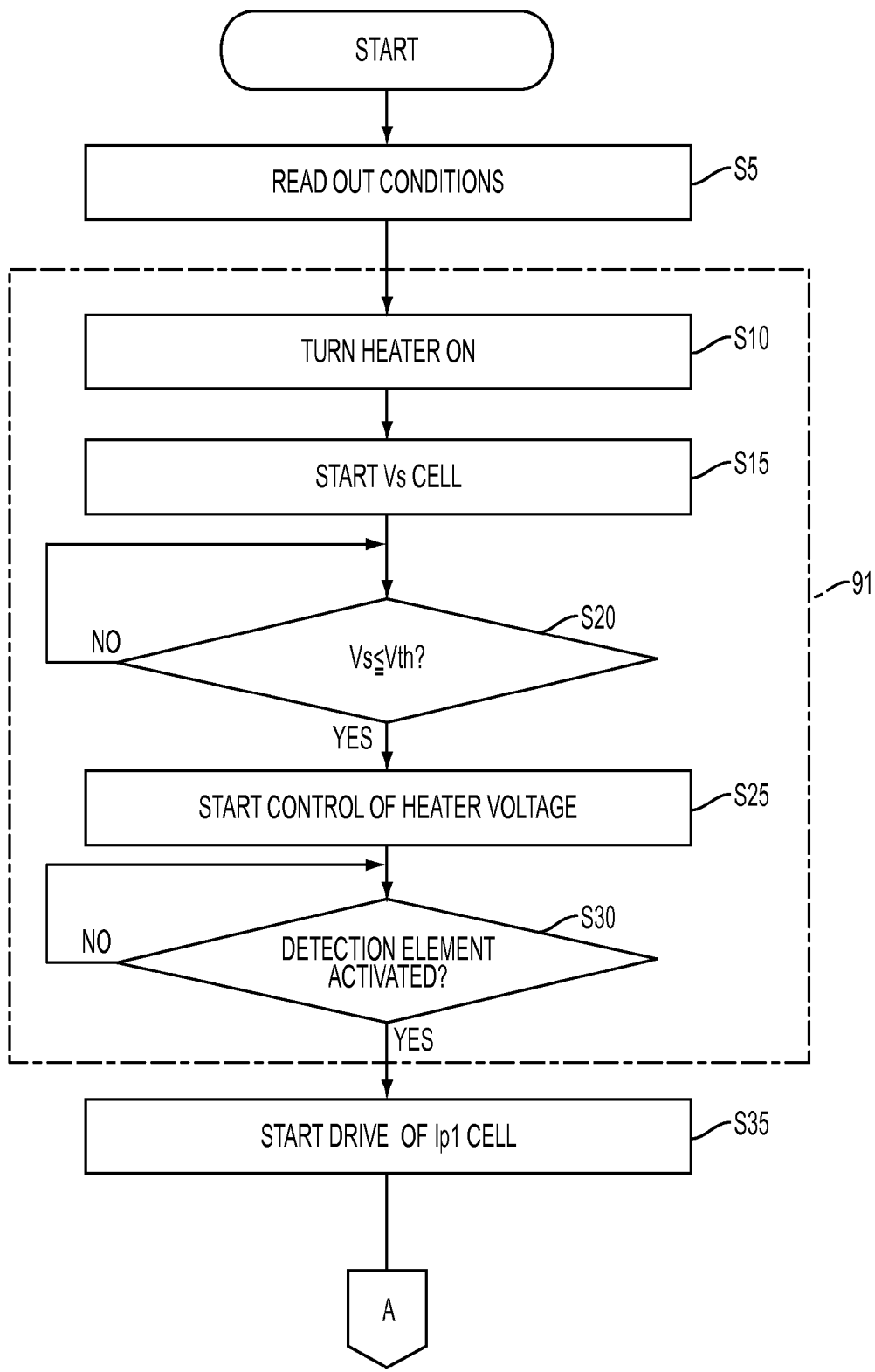
[FIGS. 12A and 12B] Flowchart of main processing according to another modification.
Figure 12B:
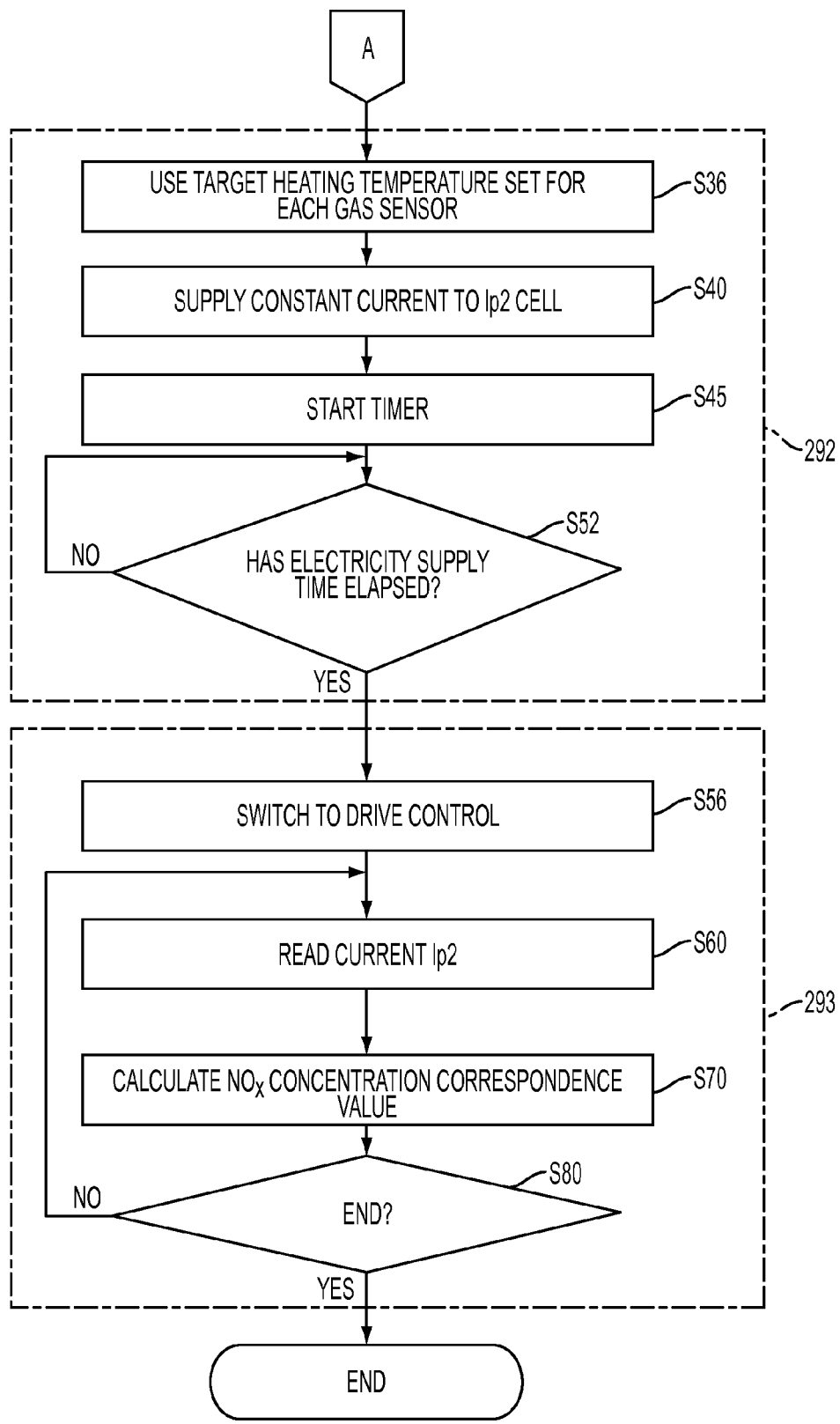

In the case where the control conditions are set in such a manner that the electricity supply time and the value of the constant current at the time of the preliminary control are set, as common control conditions, for all the gas sensors 10, and the target heating temperature of the gas sensor 10 is set for each gas sensor 10, the following processing may be executed, for example, in the main processing shown in FIGS. 12A and 12B. In FIGS. 12A and 12B, steps identical to the steps of the main processing of FIGS. 2A and 2B are denoted by the same step numbers. The main processing of FIGS. 12A and 12B differs from the main processing of FIGS. 2A and 2B in S36 and S52 of the preliminary control processing within a two-dot chain line 292, and S56 of the drive control processing within a two-dot chain line 293. Description of the steps of the main processing of FIGS. 12A and 12B similar to those of the main processing of FIGS. 2A and 2B will be omitted. In S36, the CPU 61 executes processing of starting the control of heater voltage such that the temperature of the gas sensor 10 reaches the target heating temperature set for each gas sensor 10. In S36, a temperature which is higher than a heating temperature corresponding to the target value of the internal resistance Rpvs of the Vs cell 3 set in S25, or a temperature which is equal to or lower than the heating temperature corresponding to the target value may be set as the target heating temperature in accordance with the output characteristic of the gas sensor 10. In S52, the CPU 61 waits until the electricity supply time commonly set among the gas sensors 10 elapses after the timer circuit was started in S45 (S52: NO). When the electricity supply time has elapsed after the timer circuit was started (S52: YES), the CPU 61 executes the drive control processing. Furthermore, in S56, processing of returning the target heating temperature to that set in S25 is performed in addition to the processing similar to that of S55 of FIGS. 2A and 2B. In the modification in which the target heating temperature of the gas sensor 10 is set as the control conditions, the heater conductor 38 corresponds to the heater of the present invention, and the heater drive circuit 59 corresponds to the heater drive section of the present invention. The processing of S36 to S50 corresponds to the preliminary control of the present invention, and the CPU 61, which executes the processing of S36 to S50, functions as the preliminary control means of the present invention. Notably, although the heater drive circuit 59 is provided in the control section 5, the heater drive circuit 59 may be provided in the gas sensor 10, or may be provided separately from the control section 5 and the gas sensor 10.

[Evaluation Test 5]

Figure 13:
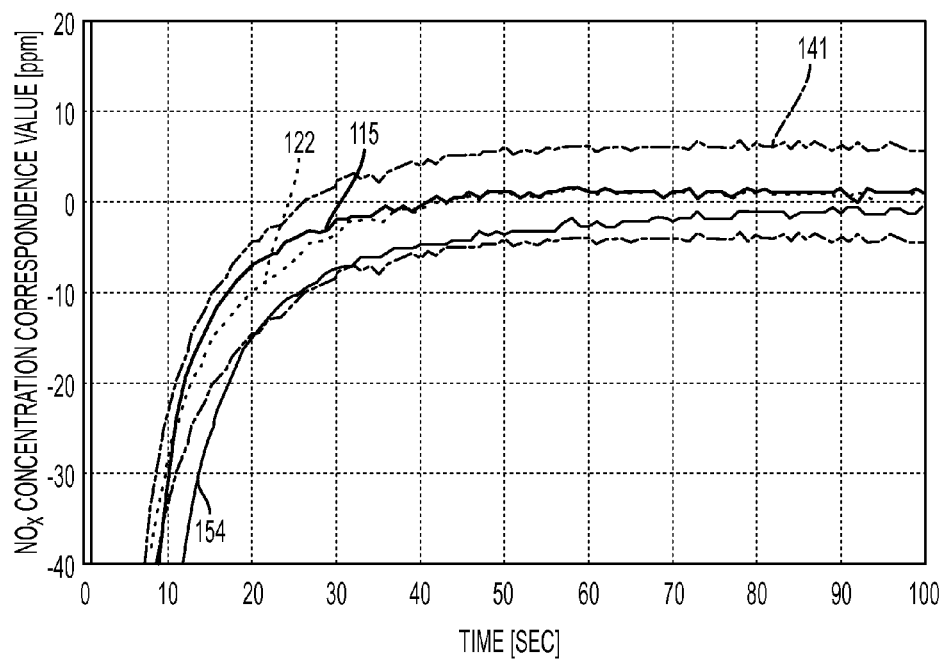
[FIG. 13] Graph representing changes with time of the $NO_X$ concentration correspondence value immediately after start of drive control for the case where preliminary control was performed under control conditions of Evaluation Test 5.

It was checked whether or not the changing pattern can be made closer to the reference pattern by means of setting the control conditions in such a manner that the target heating temperature at the time of the preliminary control is set for each gas sensor 10, and the value of the constant current and the electricity supply time at the time of the preliminary control are commonly set for the gas sensors 10. The value of the constant current at the time of the preliminary control was set to 10 μA, and the electricity supply time was set to 20 seconds. An example in which the internal resistance Rpvs of the Vs cell 3 corresponding to the target heating temperature of the gas sensor 10 in S36 was set to 300Ω was called Comparative Example, and an example in which the internal resistance Rpvs of the Vs cell 3 corresponding to the target heating temperature of the gas sensor 10 was set to 340Ω to be suited for the gas sensor 10 was called Example. Comparative Example in Evaluation Test 5 is the same as Comparative Example in Evaluation Test 4. The $NO_X$ concentration of the reference gas having the above-described composition was measured by use of the same gas sensor 10, while the preliminary control was performed under the control conditions of Comparative Example or those of Example, and a change with time in the $NO_X$ concentration correspondence value after start of the drive control processing was calculated. FIG. 13 shows the results of Evaluation Test 5. In FIG. 13, the horizontal axis represents the time elapsed after start of the drive control processing (unit: sec), and the vertical axis represents the $NO_X$ concentration correspondence value (unit: ppm).

As shown FIG. 13, in Evaluation Test 5, as in Evaluation Test 4, the target range 141 was set to a ±5 ppm range of the reference pattern 123. Both the pattern 154 of Comparative Example and the pattern 115 of Example rose from the negative side, and showed that the $NO_X$ concentration correspondence value sharply increased until 30 sec elapsed after start of the drive control processing, and increased gently after that. In the case of Comparative Example, 21 sec was required for the $NO_X$ concentration correspondence value to fall within the target range 141. In contrast, in the case of Example, 11 sec was required for the $NO_X$ concentration correspondence value to fall within the target range 141. That is, like the pattern 115 of Example, the pattern 155 of Comparative Example can be made closer to the reference pattern 123 by means of setting the target heating temperature at the time of the preliminary control for each gas sensor 10. The results of Evaluation Test 5 show that, by means of setting the target heating temperature at the time of the preliminary control (among the control conditions) for each gas sensor 10, the variation in the $NO_X$ concentration correspondence value immediately after start of the drive control processing after the preliminary control among the gas sensors 10 can be reduced.

Figure 14A:
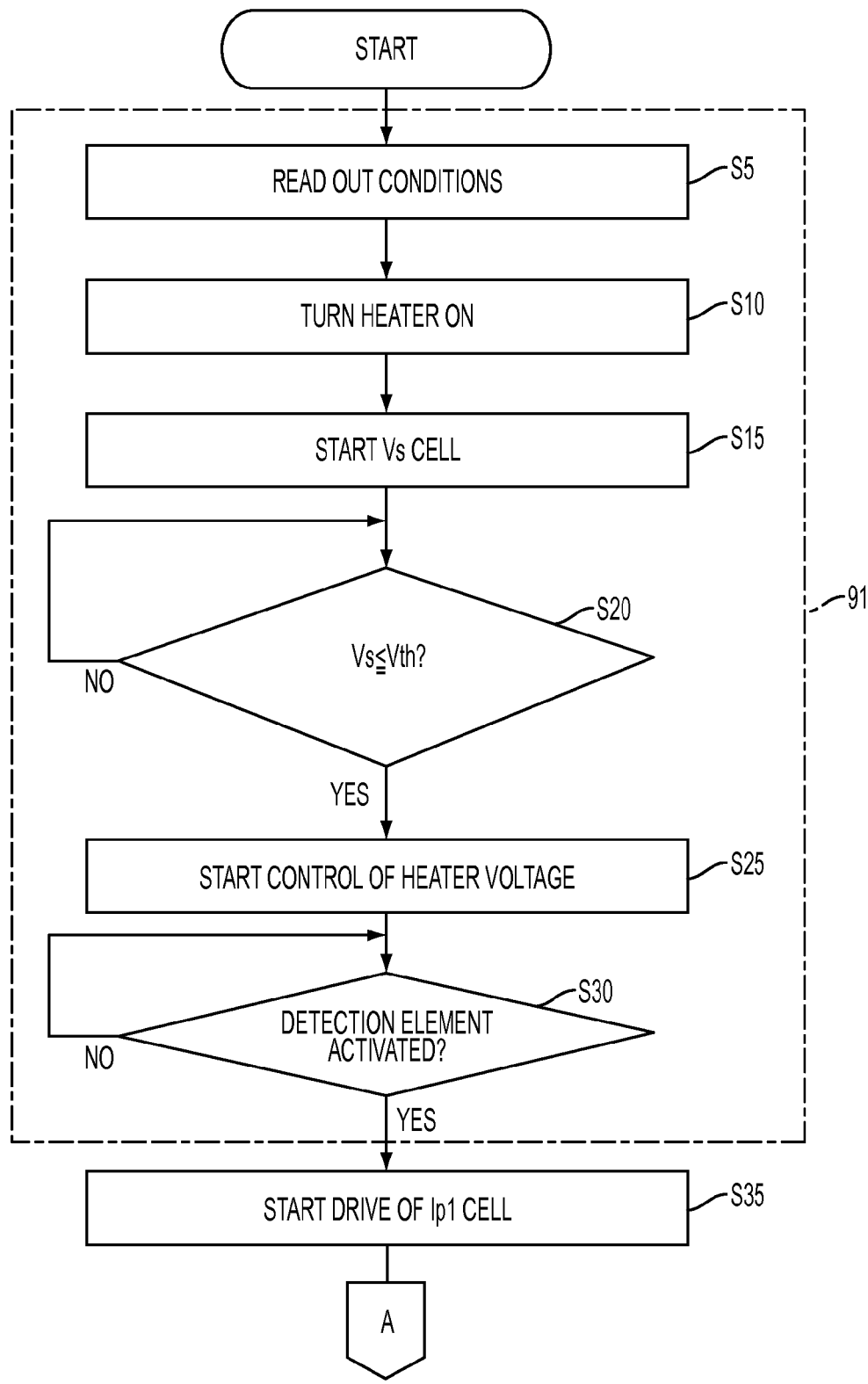
[FIGS. 14A and 14B] Flowchart of main processing according to another modification.
Figure 14B:
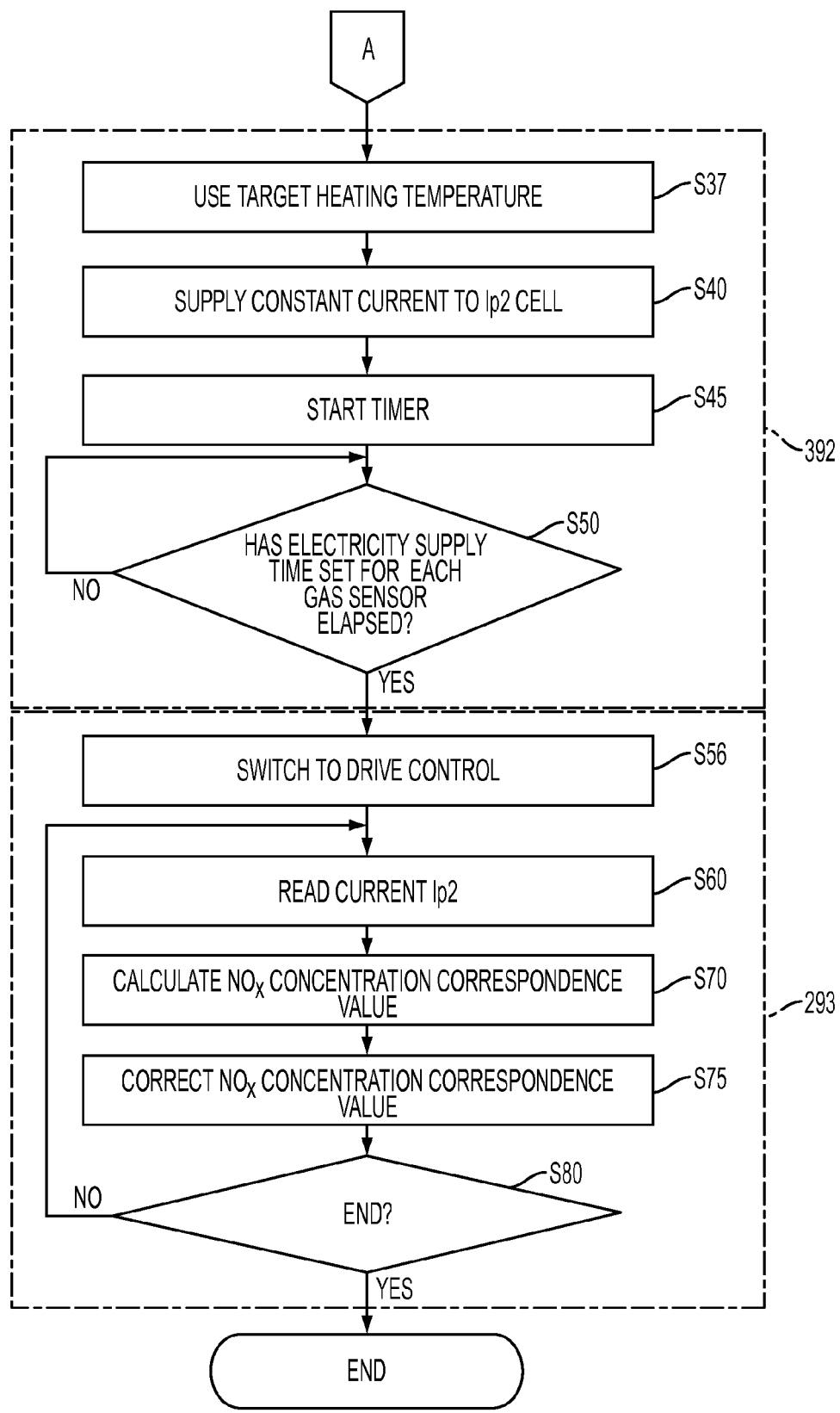

The conditions commonly set among the gas sensors 10 at the time of the preliminary control may be changed freely. For example, in the above-described second embodiment, the target heating temperature of the gas sensor 10 commonly set among the gas sensors 10 at the time of execution of the preliminary control may be set to be higher than the target value of the heating temperature of the gas sensor 10 set at the time of the activation processing or the drive control processing. In the case of this medication, the startup time, including the preliminary electricity supply time, can be shortened as compared with the second embodiment. In the case where the control conditions are set in such a manner that the value of the constant current at the time of the preliminary control and the target heating temperature of the gas sensor 10 are set, as common control conditions, for all the gas sensors 10, and the target heating temperature of the gas sensor 10 at the time of the preliminary control is rendered higher than that at the time of the drive control processing, the following processing may be executed, for example, in the main processing shown in FIGS. 14A and 14B. In FIGS. 14A and 14B, steps identical to the steps of the main processing of FIGS. 2A and 2B are denoted by the same step numbers. The main processing of FIGS. 14A and 14B differs from the main processing of FIGS. 2A and 2B in S37 of the preliminary control processing within a two-dot chain line 392, and S56 of the drive control processing within the two-dot chain line 293. Description of the steps of the main processing of FIGS. 14A and 14B similar to those of the main processing of FIGS. 2A and 2B will be omitted. In S37, the CPU 61 executes processing of starting the control of heater voltage such that the temperature of the gas sensor 10 reaches the target heating temperature common among the gas sensors 10. The target heating temperature of the gas sensor 10 in S37 is higher than that at the time of the drive control processing (the activation processing). The internal resistance Rpvs corresponding to the target heating temperature common among the gas sensors 10 is 140Ω, for example. When the internal resistance Rpvs is 140Ω, the temperature of the Vs cell 3 is estimated to be about 840° C. In S56, as in the case of FIGS. 12A and 12B, processing of returning the target heating temperature to that set in S25 is performed in addition to the processing similar to that of S55 of FIGS. 2A and 2B.

[Evaluation Test 6]

Figure 15:
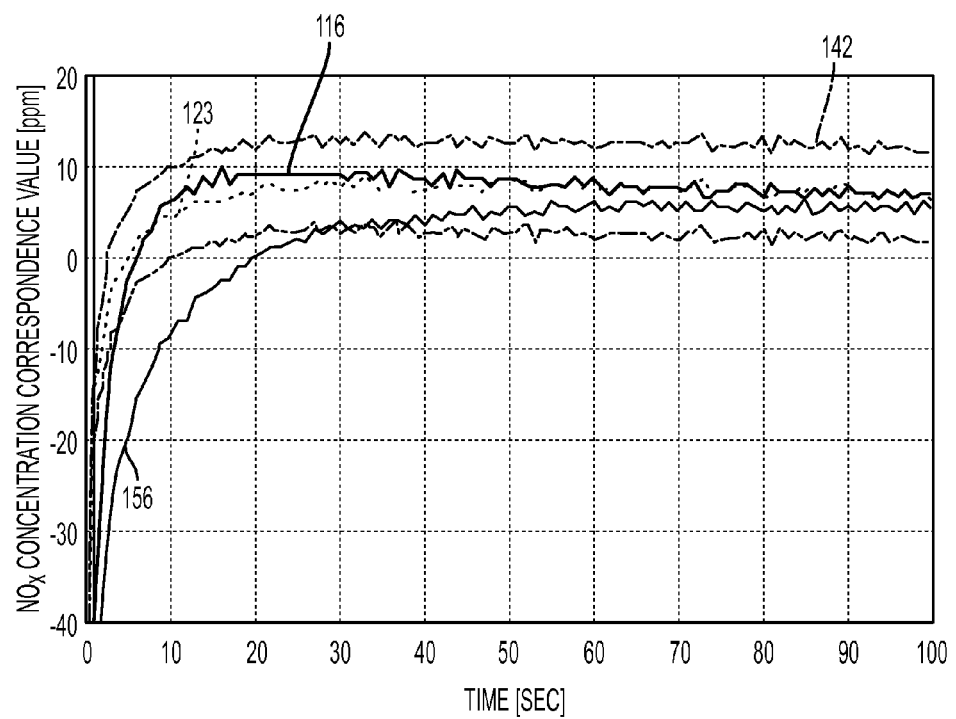
[FIG. 15] Graph representing changes with time of the $NO_X$ concentration correspondence value immediately after start of drive control for the case where preliminary control was performed under control conditions of Evaluation Test 6.

For the case where the electricity supply time at the time of execution of the preliminary control is set, as a control condition, for each gas sensor 10, it was confirmed that, by means of setting the target heating temperature at the time of the preliminary control to be higher than the target value at the time of the activation processing, the startup time, including the preliminary electricity supply time, can be shortened. The value of the constant current at the time of the preliminary control was set to 10 μA, the internal resistance Rpvs of the Vs cell 3 corresponding to the target heating temperature of the gas sensor 10 in S37 was set to 140Ω. An example in which the electricity supply time at the time of the preliminary control was 7 sec was called Comparative Example, and an example in which the electricity supply time at the time of the preliminary control was set to 5 sec to be suited for the gas sensor 10 was called Example. The $NO_X$ concentration of the reference gas having the above-described composition was measured by use of the same gas sensor 10, while the preliminary control was performed under the control conditions of Comparative Example or those of Example, and a change with time in the $NO_X$ concentration correspondence value after start of the drive control processing was calculated. FIG. 15 shows the results of Evaluation Test 6. In FIG. 15, the horizontal axis represents the time elapsed after start of the drive control processing (unit: sec), and the vertical axis represents the $NO_X$ concentration correspondence value (unit: ppm).

Although not illustrated, a variation in the changing pattern when the electricity supply time at the time of the preliminary control was changed was compared between the case where the internal resistance Rpvs of the Vs cell 3 of the gas sensor 10 at the time of the preliminary control was set to 140Ω and the case where the internal resistance Rpvs was set to 300Ω as in the above-described embodiment. The results of the comparison show that, in the case where the internal resistance Rpvs of the Vs cell 3 at the time of the preliminary control was set to 140Ω, the variation in the changing pattern when the electricity supply time at the time of the preliminary control was set to about 7 sec was small, as compared with the case where the internal resistance Rpvs was set to 300Ω. Accordingly, in the case where the electricity supply time at the time of the preliminary control was set for each gas sensor 10, by means of setting the target heating temperature at the time of execution of the preliminary control to be higher than the target value at the time of the drive control processing, it was possible to set the target range such that the change of the $NO_X$ concentration correspondence value become gentle at a relatively early stage after start of the drive control, as exemplified by a target range 142 of FIG. 15. The target range 142 is a ±5 ppm range of the reference pattern 123. In the case of a pattern 156 of Comparative Example, 34 sec was required for the $NO_X$ concentration correspondence value to fall within the target range 142. In contrast, in the case of a pattern 116 of Example, 5 sec was required for the $NO_X$ concentration correspondence value to fall within the target range 142. In the case where the pattern 116 was corrected in S75 of FIGS. 14A and 14B by use of data representing the reference pattern 123 as correction data, although not illustrated, the pattern 116 fell within the range of ±2.5 ppm when 5 sec elapsed after start of the drive control. In the case of the above-described second embodiment, the startup time, including the electricity supply time at the time of the preliminary control, was 22 sec. In contrast, in the case of the pattern 116 of Example, the startup time was 10 sec. The results of Evaluation Test 6 show that, when the target heating temperature of the gas sensor 10 commonly set among the gas sensors 10 at the time of the preliminary control is set to be higher than that at the time of the drive control processing (the activation processing), the startup time, including the preliminary electricity supply time, can be shortened.

(5) The main processing of the above-described embodiments may be changed freely. For example, the processing of correcting the $NO_X$ concentration correspondence value by use of the correction data in S70 of FIGS. 8A and 8B may be executed over the entire period in which the drive control processing is executed, or may be executed only in a period before the $NO_X$ concentration correspondence value before being corrected falls within a predetermined range. In the case where the processing of correcting the $NO_X$ concentration correspondence value by use of the correction data is executed only in a period before the $NO_X$ concentration correspondence value before being corrected falls within the predetermined range, the processing executed in a period in which correction is unnecessary can be simplified, as compared with the case where the processing of correcting the $NO_X$ concentration correspondence value is executed over the entire period in which the drive control processing is executed. Moreover, the $NO_X$ concentration correspondence value calculated in S70 of FIGS. 2A and 2B may be any value which represents the concentration of a specific gas contained in the object gas. For example, the $NO_X$ concentration correspondence value may be a digital value obtained from an analog signal representing the current flowing through the Ip2 cell 4.

(6) The method of setting the target range can be freely changed, so long as the target range is determined in consideration of an allowable range set for the variation in the concentration correspondence value after start of the drive control processing. In the above-described embodiments, the target range is determined such that changing patterns fall within the target range. However, the target range may be determined on the basis of the range of the $NO_X$ concentration correspondence value after a predetermined time (e.g., 20 sec) has elapsed after start of the drive control processing.

DESCRIPTION OF REFERENCE NUMERALS

1: sensor control apparatus
2: first oxygen pump cell
4: second oxygen pump cell
5: control section
10: gas sensor
12, 13, 14: solid electrolyte body
17, 18, 21, 22, 27, 28: electrode
23: first measurement chamber
30: second measurement chamber
40, 70: connector section
51: reference voltage comparison circuit
52: Ip1 drive circuit
53: Vs detection circuit
54: Icp supply circuit
57: Vp2 application circuit
58: constant current circuit
60: microcomputer
61: CPU
63: ROM

The invention claimed is:

1. A sensor control apparatus comprising:
a gas sensor including a first measurement chamber into which an object gas is introduced, a first oxygen pump cell having a first solid electrolyte layer and paired first electrodes provided on the inside and outside, respectively, of the first measurement chamber, a second measurement chamber communicating with the first measurement chamber, and a second oxygen pump cell having a second solid electrolyte layer and paired second electrodes provided on the inside and outside, respectively, of the second measurement chamber; and
a control section including a drive circuit section configured to perform drive control for adjusting an oxygen concentration of the object gas introduced into the first measurement chamber through supply of electricity to the first oxygen pump cell and for applying an ordinary voltage to the second oxygen pump cell, and calculation means programmed to calculate a concentration correspondence value which represents a concentration of a specific gas, on the basis of the magnitude of current flowing through the second oxygen pump cell to which the ordinary voltage is applied,
the drive circuit section further includes a constant current circuit,
the sensor control apparatus being characterized in that
the control section further includes preliminary control means programmed to perform, before start of the drive control and at the time that the drive circuit section performs drive control for adjusting the oxygen concentration of the object as introduced into the first measurement chamber through supply of electricity to the first oxygen pump cell, preliminary control which supplies a constant current to the second oxygen pump cell over a constant time, to thereby control to a constant level an amount of oxygen pumped out from the second measurement chamber to the outside of the second measurement chamber; and
the sensor control apparatus further includes a storage means configured for storing control conditions of the sensor control apparatus which are associated with the amount of the pumped oxygen and are determined for the gas sensor individually, the control conditions being determined to bring into a target range the concentration correspondence value calculated by the calculation means after start of the drive control which is started after the preliminary control is executed in a state in which a reference gas having a known concentration is introduced into the gas sensor, wherein
the preliminary control means programmed to execute the preliminary control under the control conditions,
wherein the control conditions include at least one of the constant current and the constant time determined for the gas sensor individually.

2. A sensor control apparatus according to claim 1, further comprising a heater for heating the gas sensor, and a heater control section which controls the supply of electricity to the heater, wherein
the control conditions include a target heating temperature of the gas sensor determined for the gas sensor individually; and
the preliminary control means programmed to control the heater control section, to thereby control a temperature of the gas sensor to the target heating temperature set as the control conditions.

3. A method of controlling a sensor control apparatus comprising:
a gas sensor including a first measurement chamber into which an object gas is introduced, a first oxygen pump cell having a first solid electrolyte layer and paired first electrodes provided on the inside and outside, respectively, of the first measurement chamber, a second measurement chamber communicating with the first measurement chamber, and a second oxygen pump cell having a second solid electrolyte layer and paired second electrodes provided on the inside and outside, respectively, of the second measurement chamber; and
a control section which executes a drive control step for adjusting an oxygen concentration of the object gas introduced into the first measurement chamber through supply of electricity to the first oxygen pump cell and for applying an ordinary voltage to the second oxygen pump cell, and a calculation step for calculating a concentration correspondence value which represents a concentration of a specific gas, on the basis of the magnitude of current flowing through the second oxygen pump cell to which the ordinary voltage is applied,
the method comprising:
a preliminary control step of performing, before start of the drive control step, preliminary control which supplies a constant current to the second oxygen pump cell over a constant time, to thereby control to a constant level an amount of oxygen pumped out from the second measurement chamber to the outside of the second measurement chamber; and
a read-out step of reading, out of storage means, control conditions of the sensor control apparatus which are associated with the amount of the pumped oxygen and are set for the gas sensor individually, the control conditions being determined to bring into a target range the concentration correspondence value calculated in the calculation step after start of the drive control which is started after the preliminary control is executed in a state in which a reference gas having a known concentration is introduced into the gas sensor, wherein
in the preliminary control step, the preliminary control is executed under the control conditions.

4. A method of controlling a sensor control apparatus according to claim 3,
wherein the control conditions include at least one of the constant current and the constant time determined for the gas sensor individually.

5. A method of controlling a sensor control apparatus according to claim 3, wherein the sensor control apparatus further comprises a heater for heating the gas sensor, and a heater control section which controls the supply of electricity to the heater, wherein
the control conditions include a target heating temperature of the gas sensor determined for the gas sensor individually; and
the preliminary control means controls the heater control section, to thereby control a temperature of the gas sensor to the target heating temperature set as the control conditions.

6. A method of controlling a sensor control apparatus according to claim 3,
wherein the storage means further stores, as correction data common among a plurality of the gas sensors having the same configuration, pattern data which represents a change with time in the concentration correspondence value after the drive control is started after execution of the preliminary control in a state in which the reference gas having a known concentration is introduced into the gas sensor; and the control section further includes correction means for correcting the concentration correspondence value by use of the correction data after the drive control is started.

7. A sensor control apparatus according to claim 1, wherein the storage means is configured to further store correction data common among a plurality of the gas sensors having the same configuration, pattern data which represents a change with time in the concentration correspondence value after the drive control is started after execution of the preliminary control in a state in which the reference gas having a known concentration is introduced into the gas sensor; and the control section further includes correction means programmed to correct the concentration correspondence value by use of the correction data after the drive control is started.

\* \* \* \* \*